(12) United States Patent
Coria et al.

(10) Patent No.: US 11,459,575 B2
(45) Date of Patent: Oct. 4, 2022

(54) **IMMUNOMODULATING AND IMMUNOSTIMULATING ECOTIN POLYPEPTIDES FROM *SALMONELLA* FOR DRUG-DELIVERY**

(71) Applicants: CONSEJO NACIONAL DE INVESTIGACIONES CIENTÍFICAS Y TÉCNICAS (CONICET), Ciudad Autónoma de Buenos Aires (AR); UNIVERSIDAD NACIONAL DE GENERAL SAN MARTÍN, Pcia. de Buenos Aires (AR)

(72) Inventors: Mirta L. Coria, San Martín (AR); Karina A. Pasquevich, Ciudad Autónoma de Buenos Aires (AR); Juliana Cassataro, Ciudad Autónoma de Buenos Aires (AR)

(73) Assignees: CONSEJO NACIONAL DE INVESTIGACIONES CIENTÍFICAS Y TÉCNICAS (CONICET, Ciudad Autónoma de Buenos Aires (AR); UNIVERSIDAD NACIONAL DE GENERAL SAN MARTIN, De Buenos Aires (AR)

(*) Notice: Subject to any disclaimer, the term of this patent is extended or adjusted under 35 U.S.C. 154(b) by 7 days.

(21) Appl. No.: 16/968,528

(22) PCT Filed: Feb. 8, 2019

(86) PCT No.: PCT/IB2019/051026
§ 371 (c)(1),
(2) Date: Aug. 7, 2020

(87) PCT Pub. No.: WO2019/155415
PCT Pub. Date: Aug. 15, 2019

(65) Prior Publication Data
US 2021/0093716 A1 Apr. 1, 2021

Related U.S. Application Data

(60) Provisional application No. 62/628,724, filed on Feb. 9, 2018.

(51) Int. Cl.
| | | |
|---|---|---|
| A61K 39/02 | (2006.01) |
| A61K 39/39 | (2006.01) |
| A61P 37/04 | (2006.01) |
| C07K 14/255 | (2006.01) |
| C12N 15/79 | (2006.01) |
| A61K 39/112 | (2006.01) |
| A61K 9/00 | (2006.01) |
| A61K 39/395 | (2006.01) |
| A61K 39/00 | (2006.01) |

(52) U.S. Cl.
CPC .......... *C12N 15/79* (2013.01); *A61K 39/0275* (2013.01); *A61K 39/39* (2013.01); *A61P 37/04* (2018.01); *C07K 14/255* (2013.01); *A61K 9/0029* (2013.01); *A61K 9/0053* (2013.01); *A61K 39/3955* (2013.01); *A61K 2039/55516* (2013.01)

(58) Field of Classification Search
CPC .............. C07K 14/255; A61K 39/0275; A61K 39/39; A61K 2039/55516; A61P 37/04
See application file for complete search history.

(56) References Cited

FOREIGN PATENT DOCUMENTS

| WO | WO-02/36611 A2 | 5/2002 |
| WO | WO-2012/049662 A1 | 4/2012 |

OTHER PUBLICATIONS

Eggers et al, 2004. Biochem J. 379: 107-118.*
Arumumgam et al, 2008. J Biomol. 40:213-217.*
Filipek et al, 2003. J Biol Chem. 278(42): 40959-40966.*
Simmons, C.P. et al., "Immunomodulation Using Bacterial Enterotoxins", Frontlines—Topic Review, Blackwell Science Ltd., Scandinavian Journal of Immunology, vol. 53, Dec. 23, 2001, pp. 218-226 (XP-055583629) Retrieved from the Internet: URL:https://onlinelibrary.wiley.com/doi/full/10.1046/j.1365-3083.2001.00884.
Pavot, V., et al.; New insights in mucosal vaccine development; 2012, *Vaccine;* 30; pp. 142-154.
Holmgren, J., et al.; Mucosal immunity and vaccines; Apr. 2005; *Nature Medicine;* vol. 11; pp. S45-53.
Mowat, A. M.; Anatomical basis of tolerance and immunity to intestinal antigens; Apr. 2003; *Nature Reviews: Immunology;* 3; pp. 331-341.
Reed, S. G., et al.; New horizons in adjuvants for vaccine development; Dec. 2009; *Trends Immunology;* 30; pp. 23-32.

\* cited by examiner

*Primary Examiner* — Zachary C Howard
(74) *Attorney, Agent, or Firm* — Muncy, Geissler, Olds & Lowe, P.C.

(57) ABSTRACT

The present invention relates to modified bacterial polypeptides having immunomodulatory and immunostimulatory activity. Most specifically, the present invention relates to modified bacterial polypeptides having an amino acid sequence selected from SEQ ID NO. 1, SEQ ID NO. 2, SEQ ID NO. 3, SEQ ID NO. 4 and SEQ ID NO. 5. The modified polypeptides are the adjuvant components of a pharmaceutical composition for eliciting an immune response against an specific antigen present in the pharmaceutical composition. In a preferred embodiment, the invention provides a pharmaceutical composition for a vaccine which comprises an adjuvant component which is any one of the modified polypeptides, one or more antigens, together with a pharmaceutically acceptable excipient.

Figure 1:
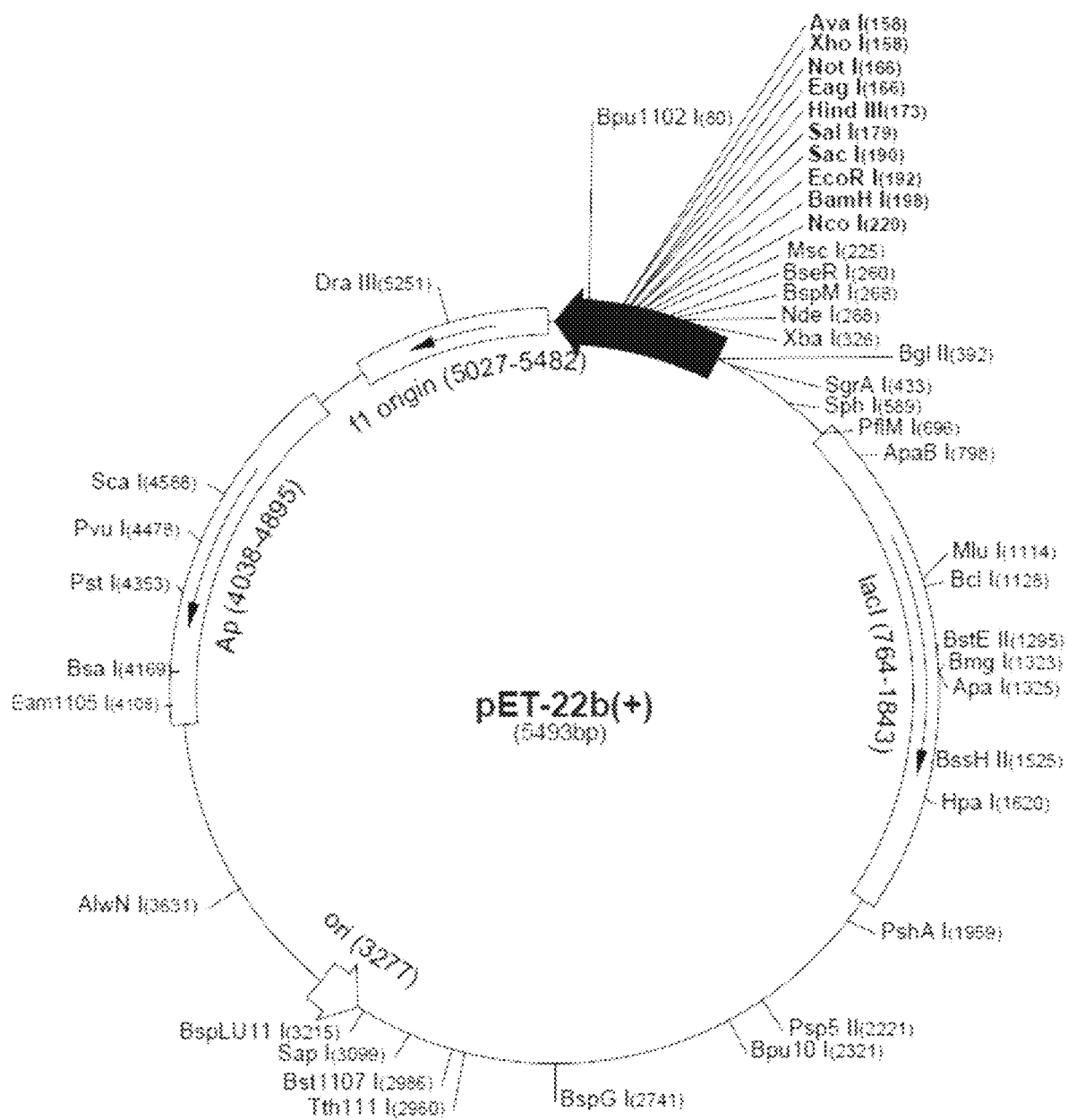

6 Claims, 19 Drawing Sheets
Specification includes a Sequence Listing.

anti-CT antibody responses
7 days after second immunization anti-CT antibody responses
7 days after third immunization DTH response

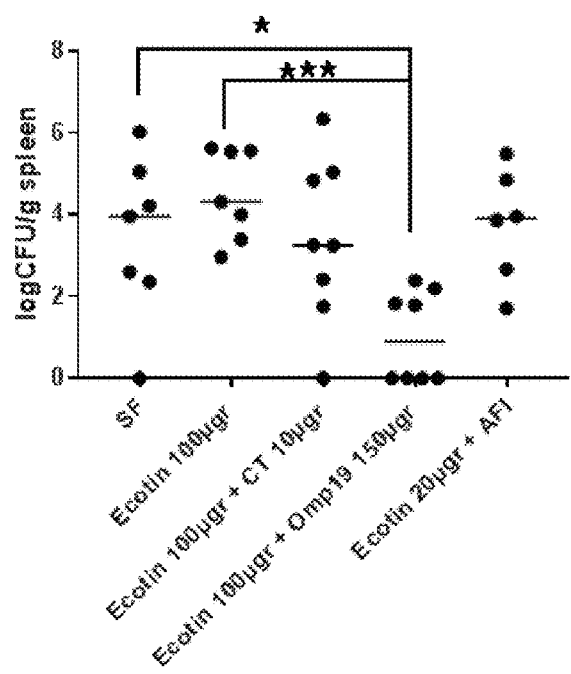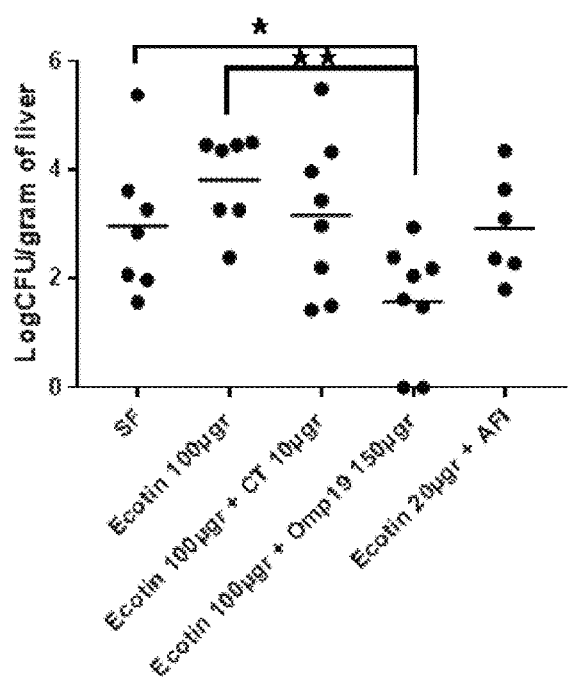
Fig. 17A                     Fig. 17B

SEQUENCE LISTING

<160> NUMBER OF SEQ ID NOS: 10

<210> SEQ ID NO 1
<211> LENGTH: 154
<212> TYPE: PRT
<213> ORGANISM: Artificial Sequence
<220> FEATURE:
<223> OTHER INFORMATION: Modified Ecotin from Salmonella enterica without signal peptide

<400> SEQUENCE: 1

```
Met Ala Asn Asn Gly Asp Thr Ala Gln Pro Leu Glu Lys Ile Ala Pro
1               5                   10                  15

Tyr Pro Gln Ala Glu Lys Gly Met Lys Arg Gln Val Ile Thr Leu Thr
            20                  25                  30

Pro Gln Gln Asp Glu Ser Thr Leu Lys Val Glu Leu Leu Ile Gly Gln
        35                  40                  45

Thr Leu Asn Val Asp Cys Asn Gln His Arg Leu Gly Gly Thr Leu Glu
    50                  55                  60

Thr Lys Thr Leu Glu Gly Trp Gly Tyr Asp Tyr Tyr Val Phe Asp Asn
65                  70                  75                  80

Val Thr Ser Pro Val Ser Thr Met Met Ala Cys Pro Glu Gly Lys Lys
                85                  90                  95

Glu Gln Lys Phe Val Thr Ala Trp Leu Gly Glu Asp Gly Met Leu Arg
            100                 105                 110

Tyr Asn Ser Lys Leu Pro Ile Val Val Tyr Thr Pro Ala Asn Val Asp
        115                 120                 125

Val Lys Tyr Arg Ile Trp Lys Ala Asp Ala Asn Val Gln Asn Ala Val
    130                 135                 140

Ala Arg Leu Glu His His His His His His
145                 150
```

<210> SEQ ID NO 2
<211> LENGTH: 116
<212> TYPE: PRT
<213> ORGANISM: Artificial Sequence
<220> FEATURE:
<223> OTHER INFORMATION: Modified aprin from Pseudomonas aeruginosa without signal peptide

<400> SEQUENCE: 2

```
Met Ala Ser Ser Leu Ile Leu Leu Ser Ala Ser Asp Leu Ala Gly Gln
1               5                   10                  15

Trp Thr Leu Gln Gln Asp Glu Ala Pro Ala Ile Cys His Leu Glu Leu
            20                  25                  30

Arg Asp Ser Glu Val Ala Glu Ala Ser Gly Tyr Asp Leu Gly Gly Asp
        35                  40                  45

Thr Ala Cys Leu Thr Arg Trp Leu Pro Ser Pro Arg Ala Trp
    50                  55                  60

Pro Thr Pro Ala Gly Ile Ala Leu Leu Glu Arg Gly Leu Thr Leu
65                  70                  75                  80

Met Leu Leu Gly Arg Gln Gly Glu Gly Asp Tyr Arg Val Gln Lys Gly
                85                  90                  95
```

Asp Gly Gly Gln Leu Val Leu Arg Arg Ala Thr Pro Leu Glu His His
            100                 105                 110

His His His His
        115

<210> SEQ ID NO 3
<211> LENGTH: 115
<212> TYPE: PRT
<213> ORGANISM: Artificial Sequence
<220> FEATURE:
<223> OTHER INFORMATION: Modified Staphostatin B from Staphylococcus
      aureus

<400> SEQUENCE: 3

Met His His His His His His Tyr Gln Leu Gln Phe Ile Asn Leu Val
1               5                   10                  15

Tyr Asp Thr Thr Lys Leu Thr His Leu Glu Gln Thr Asn Ile Asn Leu
            20                  25                  30

Phe Ile Gly Asn Trp Ser Asn His Gln Leu Gln Lys Ser Ile Cys Ile
        35                  40                  45

Arg His Gly Asp Asp Thr Ser His Asn Gln Tyr His Ile Leu Phe Ile
    50                  55                  60

Asp Thr Ala His Gln Arg Ile Lys Phe Ser Ser Ile Asp Asn Glu Glu
65                  70                  75                  80

Ile Ile Tyr Ile Leu Asp Tyr Asp Asp Thr Gln His Ile Leu Met Gln
                85                  90                  95

Thr Ser Ser Lys Gln Gly Ile Gly Thr Ser Arg Pro Ile Val Tyr Glu
            100                 105                 110

Arg Leu Val
        115

<210> SEQ ID NO 4
<211> LENGTH: 114
<212> TYPE: PRT
<213> ORGANISM: Artificial Sequence
<220> FEATURE:
<223> OTHER INFORMATION: Modified Staphostatin A from Staphylococcus
      aureus

<400> SEQUENCE: 4

Met His His His His His His Glu Gln Phe Glu Leu Phe Ser Ile Asp
1               5                   10                  15

Lys Phe Lys Cys Asn Ser Glu Ala Lys Tyr Tyr Leu Asn Ile Ile Glu
            20                  25                  30

Gly Glu Trp His Pro Gln Asp Leu Asn Asp Ser Pro Leu Lys Phe Ile
        35                  40                  45

Leu Ser Thr Ser Asp Asp Ser Asp Tyr Ile Cys Lys Tyr Ile Asn Thr
    50                  55                  60

Glu His Lys Gln Leu Thr Leu Tyr Asn Lys Asn Asn Ser Ser Ile Val
65                  70                  75                  80

Ile Glu Ile Phe Ile Pro Asn Asp Asn Lys Ile Leu Leu Thr Ile Met
                85                  90                  95

Asn Ile Glu Ala Leu Gly Thr Ser Pro Arg Met Thr Phe Ile Lys His
            100                 105                 110

Lys Ser

<210> SEQ ID NO 5
<211> LENGTH: 191

```
<212> TYPE: PRT
<213> ORGANISM: Artificial Sequence
<220> FEATURE:
<223> OTHER INFORMATION: Modified serine carboxypeptidase Y inh.
      from Helicobacter pylori

<400> SEQUENCE: 5

Met Lys Thr Phe Glu Val Met Ile Gln Thr Asp Ser Glu Gly Tyr Leu
1               5                   10                  15

Asp Ala Lys Phe Gly Gly Asn Ala Pro Arg Gly Phe Leu Asn Pro Asn
            20                  25                  30

Gly Leu Pro Thr Tyr Ser Pro Lys Ile Ser Trp Gln Lys Val Glu Gly
        35                  40                  45

Ala Gln Ser Tyr Ala Leu Glu Leu Ile Asp His Asp Ala Gln Lys Val
    50                  55                  60

Cys Gly Met Ser Phe Ile His Trp Val Val Gly Asn Ile Ser His Asn
65                  70                  75                  80

Val Leu Glu Glu Asn Ala Ser Met Met Asp Lys Arg Ile Thr Gln Gly
                85                  90                  95

Val Asn Ser Leu Thr Gln Gly Phe Ile Arg Ser Pro Leu Asn Glu Ser
            100                 105                 110

Glu Lys Gln Arg Ser Asn Leu Asn Asn Ser Val Tyr Ile Gly Pro Met
        115                 120                 125

Pro Pro Asn Gly Asp His His Tyr Leu Ile Gln Val Tyr Ala Leu Asp
    130                 135                 140

Ile Pro Lys Leu Ala Leu Lys Ala Pro Phe Phe Leu Gly Asp Leu His
145                 150                 155                 160

Asp Lys Met Arg Asn His Ile Ile Ala Ile Gly Arg Lys Glu Phe Leu
                165                 170                 175

Tyr Lys Gln Phe Met Arg Lys Leu Glu His His His His His
            180                 185                 190

<210> SEQ ID NO 6
<211> LENGTH: 447
<212> TYPE: DNA
<213> ORGANISM: Artificial Sequence
<220> FEATURE:
<223> OTHER INFORMATION: Nucleotide sequence encoding modified Ecotin
      from Salmonella without signal peptide

<400> SEQUENCE: 6
catatggcta acaatggcga taccgcccag ccgctggaaa aaatcgcccc ctatccgcag     60
gcggaaaaag gaatgaagcg gcaagtgata acccttaccc ctcagcagga tgaatctacc    120
ctcaaagtgg aactgttgat tggccaaacg ctgaatgtgg attgtaacca gcatcgcctc    180
ggcggcacgc tggaaacaaa aacgctgaa  ggctggggct atgactatta tgtctttgat    240
aacgtcacct ctccggtatc aaccatgatg gcctgccctg aaggtaagaa agagcaaaaa    300
ttcgtcaccg cctggctggg tgaagacggg atgctgcgct acaacagcaa gctgccgatc    360
gtggtgtata ccccggcgaa tgtggacgtg aaataccgca tctggaaagc ggacgctaac    420
gtacagaacg ccgtcgcgcg actcgag                                        447

<210> SEQ ID NO 7
<211> LENGTH: 333
<212> TYPE: DNA
<213> ORGANISM: Artificial Sequence
<220> FEATURE:
<223> OTHER INFORMATION: Nucleotide encoding modified aprin from
      Pseudomonas aeruginosa (without signal peptide)
```

<400> SEQUENCE: 7

```
catatggcca gcagtctgat tcttctcagc gcttccgatc tcgccgggca atggaccctg    60
cagcaggacg aggcgcccgc gatctgccac ctggagctgc gcgacagcga agtggcggaa   120
gccagtggct acgacctggg cggcgatacc gcctgcctca cgcgctggct gcccagcgag   180
ccgcgcgcct ggaggcctac cccggccggg atcgcgctgc tcgaacgcgg cggcctgacc   240
ctgatgctcc tcggtcgcca gggcgagggc gactaccggg tgcagaaggg cgacggcggg   300
cagttggtgc tgcgccgcgc gacgcccctc gag                                333
```

<210> SEQ ID NO 8
<211> LENGTH: 357
<212> TYPE: DNA
<213> ORGANISM: Artificial Sequence
<220> FEATURE:
<223> OTHER INFORMATION: Nucleotide encoding modified staphostatin B
      from Staphylococcus aureus

<400> SEQUENCE: 8

```
catatgcacc accaccacca ccactatcaa ctacaattta taaatttagt ttacgacaca    60
accaaactca cacatctaga acaaaccaat atcaatttat tcattggtaa ttggagtaat   120
catcaattac aaaaatcaat ttgtatacgt catggcgatg atacaagtca caatcaatat   180
catattcttt ttatagatac ggcacatcaa cgcattaaat tttcatctat tgataatgaa   240
gaaatcattt atattcttga ttatgatgat acacagcata tcctcatgca aacgtcatcc   300
aaacaaggta ttggcacttc gcgcccaatc gtttatgagc gcttagtata actcgag      357
```

<210> SEQ ID NO 9
<211> LENGTH: 354
<212> TYPE: DNA
<213> ORGANISM: Artificial Sequence
<220> FEATURE:
<223> OTHER INFORMATION: Nucleotide encoding modified staphostatin A
      from Staphylococcus aureus

<400> SEQUENCE: 9

```
catatgcacc accaccacca ccacgaacaa tttgaattat ttagtattga taaattcaaa    60
tgtaattcag aggctaagta ttatcttaat attattgagg gagaatggca tcctcaagat   120
ttaaatgata gccctttaaa atttattctc agtacctcag acgattctga ttacatttgc   180
aaatatataa atacagaaca caaacaactc acattatata ataaaaataa tagctcaatt   240
gttattgaaa tatttatacc aaatgataat aaaaatactac taacaattat gaacatagaa   300
gctttaggaa cttctcctag aatgactttc attaagcata aaagttaact cgag         354
```

<210> SEQ ID NO 10
<211> LENGTH: 558
<212> TYPE: DNA
<213> ORGANISM: Artificial Sequence
<220> FEATURE:
<223> OTHER INFORMATION: Nucleotide encoding modified serine
      carboxypeptidase Y inhibitor from Helicobacter pylori

<400> SEQUENCE: 10

```
catatgaaaa cttttgaagt gatgattcaa accgattcag aagggtattt ggacgctaaa    60
tttggcggta acgctcctag agggtttctc aatccaaacg gcttaccac ttattcgcct   120
aaaatctcat ggcaaaaagt agaaggtgct caaagctatg cgttagaact tattgatcat   180
gacgcgcaaa aagtgtgcgg catgtcgttt atccattggg tcgtgggcaa tatctctcat   240
```

-continued

```
aatgttttag aagaaaacgc ctccatgatg gataaaagga ttactcaagg ggtcaattcg    300
cttactcaag gctttatccg ttctcctctt aatgaaagcg aaaaacaacg ctccaatctc    360
aataacagcg tctatatcgg ccccatgcct cctaatggcg atcaccatta cttgattcaa    420
gtgtatgccc tagacattcc taaactcgcc ttaaaagccc cttttttctt aggcgatttg    480
catgacaaaa tgcgcaacca tatcatcgcc atagggagaa aggaatttct atacaagcag    540
tttatgagga aactcgag                                                 558
```

IMMUNOMODULATING AND IMMUNOSTIMULATING ECOTIN POLYPEPTIDES FROM *SALMONELLA* FOR DRUG-DELIVERY

FIELD OF THE INVENTION

The present invention generally relates to polypeptides which are immunomodulators and immunostimulants. Most specifically, the present invention relates to modified bacterial polypeptides having immunomodulatory and immunostimulatory activity. Yet more specifically, the modified polypeptides of the invention are the adjuvant components of a pharmaceutical composition for eliciting an immune response against the specific antigen present in the pharmaceutical composition. In a preferred embodiment, the invention provides a pharmaceutical composition for a vaccine which comprises an adjuvant component which is any one of the modified polypeptides according to the sequence listing of the present invention, one or more antigens, together with a pharmaceutically acceptable excipient.

STATE OF THE ART

In veterinary and medical sciences, immunomodulation is an area wherein extensive studies have been conducted to devise methods to improve disease resistance as well as to prevent or control immune disorders of host by optimum regulation of the immune system. Today, most infectious diseases of man and animals are treated and controlled mainly by using broad-spectrum antibiotics and vaccines. However, the antibacterial agents are becoming increasingly ineffective due to rapid emergence of resistant microbial strains. So, there is high requirement for novel and improved alternative therapeutic and prophylactic strategies to manage several diseases which are flaring at alarming pace because of the increase in international traffic, globalization and changing food habits. Immunomodulation is focused on manipulation of immune system to control the infections and other adverse health effects with precise regulation to avoid any complications while suppressive or potentiating efforts are made to benefit the animal and human health.

The immune system can be manipulated specifically by vaccination or non-specifically by immunomodulation.

It is generally accepted that vaccination is the most efficient and cost-effective form of preventing infectious diseases. Although most vaccines currently licensed are administered by parenteral route, this vaccination strategy usually fails to elicit adequate mucosal immune responses. Thus, diseases caused by mucosal pathogens are still among the major causes of death in developing countries. It is well documented that oral immunization can generate strong protective immunity at the intestinal mucosa as well as systemic (1-5). However, oral administration of antigens faces two major issues, one being degradation of the antigen by enzymes present at the gastrointestinal tract and the other being the induction of immune tolerance against the administered antigen (6-8). Current oral vaccines based on attenuated pathogens are usually capable of bypassing these difficulties but on the other hand present important safety concerns (9). The safe alternative consists on the development of oral vaccines based on killed pathogens or subunit thereof, but this holds major challenges since they are poorly immunogenic and usually require multiple doses and the use of an effective oral adjuvant (10, 11).

Two bacterial products are being used as oral adjuvants in the mouse model, cholera toxin (CT) from *V. cholerae* and heat-labile enterotoxin (LT) from *E. coli* (12). Since enterotoxicity seriously limits the practical use of these compounds in humans, modifications have been generated to reduce this effect. A modified version of CT lacking the A subunit (CTB) is now currently licensed as part of the Dukoral® vaccine for human use (13) and also a double mutant of LT (dmLT) which retains its adjuvant properties, is under clinical trial (14). However, neither of these molecules is capable of overcoming antigen degradation in the gastrointestinal tract. Interesting strategies to address this issue include antigen delivery through intestine-targeted pH-dependent microparticles (15), biodegradable nano or microparticles (16-18) antigen targeting to M cells (19) and protease inhibitors (20). However, there is still a need for appropriate adjuvants, and delivery systems that can be orally administered.

In addition, and as aforementioned, the immune system can also be manipulated non-specifically by immunomodulation. An immunomodulator may be defined as any biological or synthetic substance that can stimulate/suppress either innate or adaptive or both arms of the immune system. Immunomodulators include both immunostimulatory and immunosuppressive agents. Immunostimulatory agents are substances capable of enhancing host defense mechanisms to provide protection against infections. Their modes of actions include augmentation of anti-infectious immunity by the cells of the immune system, encompassing lymphocyte subsets, macrophages, dendritic cells and natural killer cells.

Dendritic cells (DC) represent a sentinel-like system with the capacity to produce cytokines and chemokines, capture and process antigens, to migrate into secondary lymphoid organs, and to activate naive T lymphocytes. They can be found in all lymphoid and most non-lymphoid tissues, including mucosal surfaces, like the lung and the gut, where intricate networks of DCs are situated to sense potential harmful exposures.

Dendritic cells (DC) are main gate-keepers of the immune system, bridging the innate and adaptive immune system. DCs are able to mature into inflammatory DCs at sites of inflammation in both autoimmune and allergic disease, thereby sustaining a continuous activation of the immune system at sites of inflammation. Maturation/activation of dendritic cells (DCs) is a key step in the induction of adaptive immune responses. The modulation and manipulation of DC functions through exposure of DCs to immunomodulatory agents is an approach that could result in therapeutic benefit in many clinical situations.

SUMMARY OF THE INVENTION

The present invention provides an immunomodulating polypeptide selected from the group of modified Ecotin from *Salmonella enterica* without signal peptide of SEQ ID NO. 1, modified aprin from *Pseudomonas aeruginosa* without signal peptide, of SEQ ID NO. 2, modified staphostatin B from *Staphylococcus aureus* of SEQ ID NO. 3, modified staphostatin A from *Staphylococcus aureus* of SEQ ID NO. 4, and modified serine carboxypeptidase Y inh. from *Helicobacter pylori* of SEQ ID NO. 5.

Experimental evidence herein provided shows that each one of the polypeptides of the invention has proven to induce the activation of dendritic cells (DCs), thus being valuable immunomodulating agents.

The invention thus also concerns a pharmaceutical composition comprising (i) an immunomodulating polypeptide selected from the group of modified Ecotin from *Salmonella enterica* without signal peptide of SEQ ID NO. 1, modified aprin from *Pseudomonas aeruginosa* without signal peptide, of SEQ ID NO. 2, modified staphostatin B from *Staphylococcus aureus* of SEQ ID NO. 3, modified staphostatin A from *Staphylococcus aureus* of SEQ ID NO. 4, and modified serine carboxypeptidase Y inh. from *Helicobacter pylori* of SEQ ID NO. 5, and (ii) a pharmaceutically acceptable excipient.

Experimental evidence shows that each one of the polypeptides of the invention has proven useful as an adjuvant for orally administered antigens. Administration of the polypeptides with an antigen results in the production of serum IgG and/or mucosal IgA against the antigen. Ag-specific $CD4^+$ and $CD8^+$ T cells increase also when polypeptides are delivered.

Accordingly, an object of this invention is an immunological adjuvant for vaccines, preferably administered via the oral route, where the adjuvant is a polypeptide selected from the group of modified Ecotin from *Salmonella enterica* without signal peptide of SEQ ID NO. 1, modified aprin from *Pseudomonas aeruginosa*, of SEQ ID NO. 2, modified staphostatin B from *Staphylococcus aureus* of SEQ ID NO. 3, modified staphostatin A from *Staphylococcus aureus* of SEQ ID NO. 4, and modified serine carboxypeptidase Y inh. from *Helicobacter pylori* of SEQ ID NO. 5.

A further object of this invention is a pharmaceutical composition for stimulating protective immunity at mucosal surfaces throughout the host.

An additional object of the invention is a pharmaceutical composition for inducing a protective immune response to any antigen, wherein the composition comprises at least an antigen in combination with one or more polypeptides selected from the group of modified Ecotin from *Salmonella enterica* without signal peptide of SEQ ID NO. 1, modified aprin from *Pseudomonas aeruginosa* without signal peptide, of SEQ ID NO. 2, modified staphostatin B from *Staphylococcus aureus* of SEQ ID NO. 3, modified staphostatin A from *Staphylococcus aureus* of SEQ ID NO. 4, and modified serine carboxypeptidase Y inh. from *Helicobacter pylori* of SEQ ID NO. 5.

According to another embodiment, the composition of the invention is a component of a vaccine against any specific antigen where a specific antibody or cellular response would be useful in active acquired immunity to a particular disease.

According to another embodiment, the composition of the invention is a component of a vaccine or formulation composed of any specific antigen to which the induction of a specific immune response is required or desired.

Accordingly, the present invention provides a vaccine or formulation comprising at least an antigen and a polypeptide selected from the group of modified Ecotin from *Salmonella enterica* without signal peptide of SEQ ID NO. 1, modified aprin from *Pseudomonas aeruginosa* without signal peptide, of SEQ ID NO. 2, modified staphostatin B from *Staphylococcus aureus* of SEQ ID NO. 3, modified staphostatin A from *Staphylococcus aureus* SEQ ID NO. 4, and modified serine carboxypeptidase Y inh. from *Helicobacter pylori* of SEQ ID NO. 5, and optionally a pharmaceutically acceptable vehicle.

According to another object of the present invention, the nucleotide sequences encoding the polypeptides of the invention are also provided. Said nucleic acid sequences are selected from SEQ ID NO. 6 to 10, wherein SEQ ID NO. 6 codifies for the modified Ecotin from *Salmonella* (without signal peptide); SEQ ID NO. 7 codifies for the modified aprin from *Pseudomonas aeruginosa* (without signal peptide); SEQ ID NO. 8 codifies for the modified staphostatin B from *Staphylococcus aureus*; SEQ ID NO. 9 codifies for the modified staphostatin A from *Staphylococcus aureus*; and SEQ ID NO. 10 codifies for the modified serine carboxypeptidase Y inhibitor from *Helicobacter pylori*.

According to another object of the present invention, a method is provided for stimulating innate immune response in a subject, comprising administering to said subject an effective amount of the pharmaceutical composition comprising one or more polypeptides of the invention.

According to another object of the present invention, a method is provided for enhancing the immune response against an antigen in a subject, comprising administering to said subject an effective amount of the pharmaceutical composition or of a vaccine comprising one or more polypeptides of the invention.

Another object of the invention is a method for inducing protective (sometimes termed adaptive) immunity to an antigen by administering to a subject in need thereof at least one dose of an effective amount of an antigen and an effective amount of one or more of the polypeptides of the invention.

In particular, another object of the invention is a method for inducing protective (sometimes termed adaptive) immunity to pathogen-derived antigens by administering to a subject in need thereof at least one dose of an effective amount of a pathogen-derived antigen and an effective amount of a polypeptide selected from the group of modified Ecotin from *Salmonella enterica* without signal peptide of SEQ ID NO. 1, modified aprin from *Pseudomonas aeruginosa* without signal peptide, of SEQ ID NO. 2, modified staphostatin B from *Staphylococcus aureus* of SEQ ID NO. 3, modified staphostatin A from *Staphylococcus aureus* of SEQ ID NO. 4, and modified serine carboxypeptidase Y inh. from *Helicobacter pylori* of SEQ ID NO. 5, in an oral or parenteral acceptable pharmaceutical composition.

The antigen may consist of a peptide, protein, polysaccharide or any molecule or chemical moiety component of an organism or of a non-living organism or extract of said organism, to which the host may induce an immune response. Alternatively, the antigen may consist of substances containing epitopes shared by substances (allergens) to which the host has previously established an allergic immune response evoking allergic manifestations.

According to a preferred embodiment, the antigen is selected from the group of pathogen-derived antigens, tumor cell antigens, self-antigens and allergens. Pathogen-derived antigens may be from bacteria, virus, parasites or fungi.

According to a preferred embodiment, the pathogen-derived antigen is selected from the group of viral antigens, bacterial antigens, parasitic antigens and fungal antigens.

According to another embodiment, the antigen is an antigen of a virus selected from the group comprising, without limitation, Poxviridae, Herpesviridae, Herpes Simplex virus 1, Herpes Simplex virus 2, Adenoviridae, Papovaviridae, Enteroviridae, Picornaviridae, Papillomaviridae Parvoviridae, Reoviridae, retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotaviridae, Vaccinia virus.

According to another embodiment, the antigen is an antigen of a bacterium selected from the group comprising, without limitation *Streptococcus pyogenes, Streptococcus pneumoniae, Neisseria gonorrheae, Neisseria meningitidis, Corynebacterium diphtherias, Clostridium botulinum, Clostridium perfringens, Clostridium tetani, Hemophilus influenzae, Klebsiella pneumoniae, Klebsiella ozaenae,*

Figure 5A:
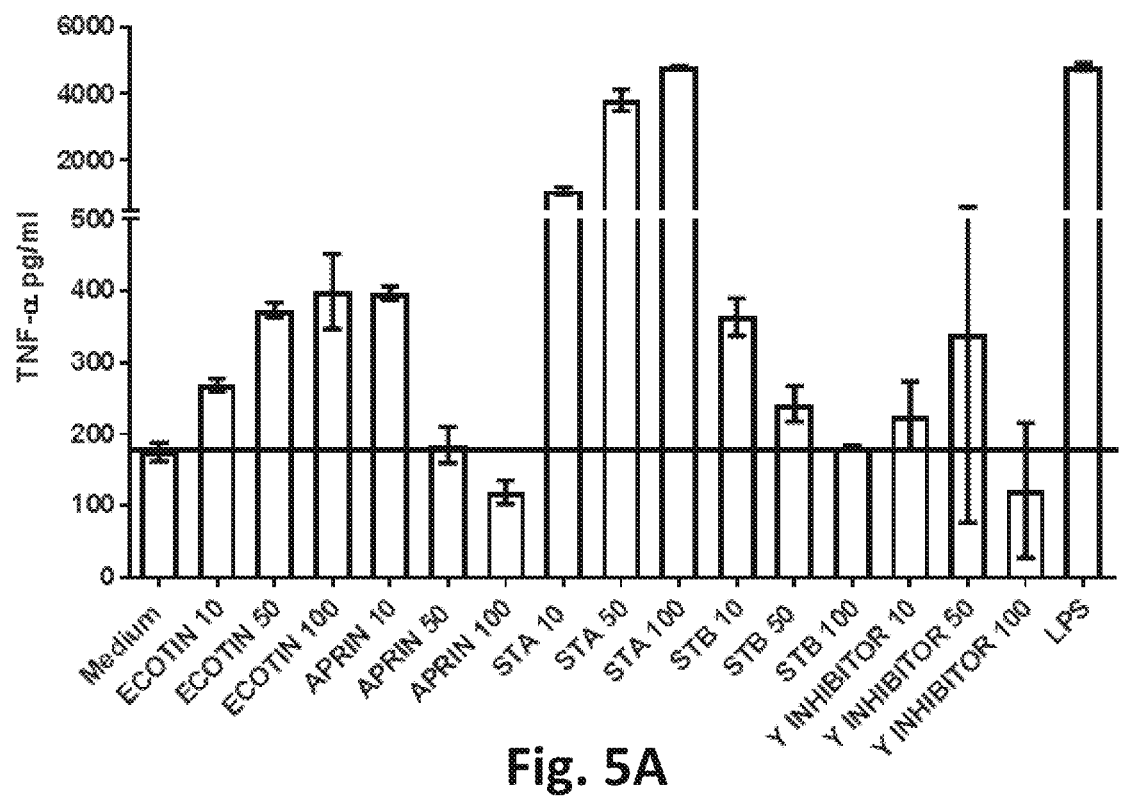
Figure 5B:
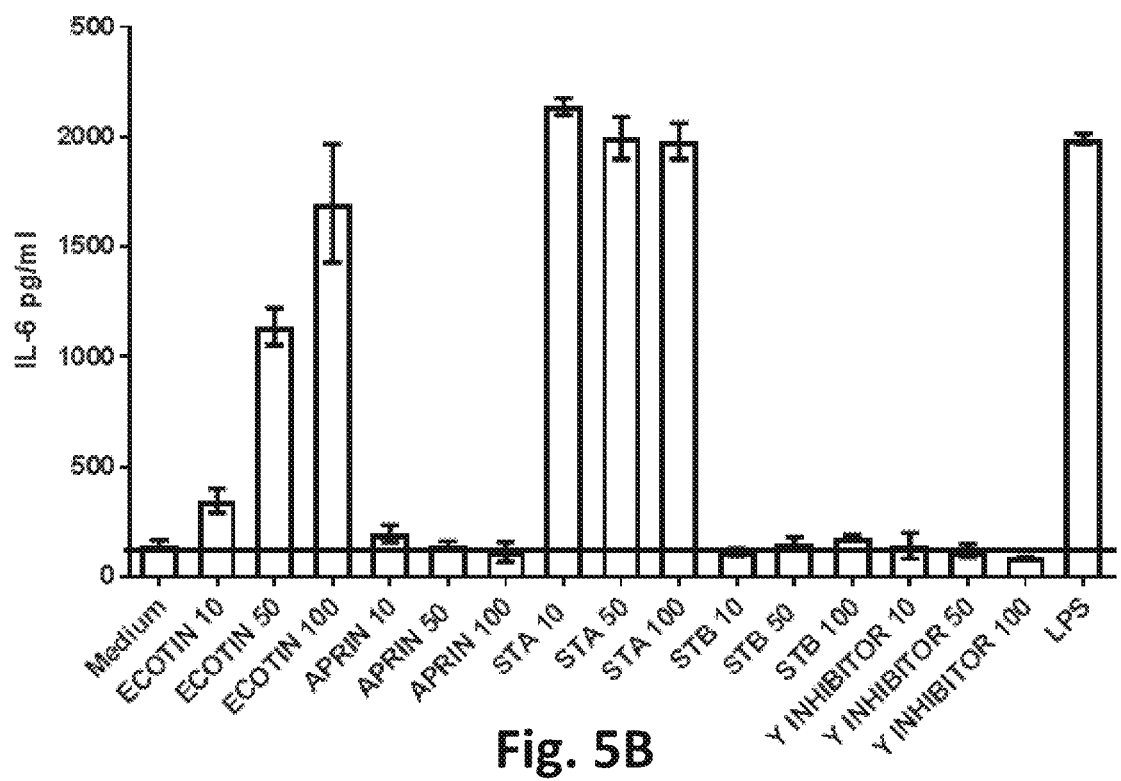

*Klebsiella rhinoscleromatis, Staphylococcus aureus, Vibrio cholerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Francisella tularensis, Brucella abortus, Brucella suis, Brucella melitensis, Mycoplasma spp., Rickettsia prowazeki, Rickettsia tsutsugamushi, Chlamydia spp, Listeria monocytogenes.*

According to another embodiment, the antigen is an antigen of a protozoan selected from the group comprising, without limitation Entomoeba *histolytica, Trichomonas tenas, Trichomonas hominis, Trichomonas vaginalis, Trypanosoma gambiense, Trypanosoma rhodesiense, Trypanosoma cruzi, Leishamania donovani, Leishamania tropica, Leishmania braziliensis, Pneumocystis pneumonia, Plasmodium vivax, Plasmodium falciparum*, and *Plasmodium* malaria.

According to another embodiment, the antigen is an antigen of a Helminth selected from the group comprising, without limitation *Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworm.

According to another embodiment, the antigen is an antigen of a fungus selected from the group comprising, without limitation *Coccidioides immitis, Aspergillus fumigatus, Candida albicans, Blastomyces dermatitidis, Cryptococcus neoformans*, and *Histoplasma capsulatum.*

According to another embodiment, the antigen is a tumor-derived antigen selected from the group including, for example, without limitation AFP (alphafetoprotein), ETA (epithelial tumor antigen), CEA (carcinoembryonic antigen), MAGE (melanoma-associated antigen), MUC-1, abnormal products of ras, p53, TPBG (trophoblast glycoprotein), CEA (colorectal carcinoma), Immature laminin receptor (RCC), TAG-72 (prostate carcinoma), HPV E6, E7 (Cervical carcinoma), BING-4 (Melanoma), Calcium-activated chloride channel 2 (Lung carcinoma), Cyclin-$B_1$ (Multi), 9D7 (RCC), Ep-CAM (Breast carcinoma), EphA3 (Multi), Her2/neu (multi), Telomerase (multi), Mesothelin (ductal pancreatic carcinoma), SAP-1 (colorectal carcinoma), surviving (multi), BAGE family (multi), CAGE family (multi), GAGE family (multi), MAGE family (multi), SAGE family (multi), XAGE family (multi), NY-ESO-1/LAGE-1 (multi), PRAME (multi), SSX-2 (melanoma, multi), Melan-A/MART-1 (melanoma), Gp100/pme117 (melanoma), Tyrosinase (melanoma), TRP-1/2 (melanoma), P. polypeptide (melanoma), MC1R (melanoma), Prostate-specific antigen (PSA, prostate), β-catenin (melanoma, prostate, HCC), BRCA1/2 (breast, ovarian carcinoma), CDK4 (multi), CML66 (CML), Fibronectin (multi), MART-2 (melanoma), p53 (multi), Ras (multi), TGF-βRII (colorectal carcinoma), MUC1 (ductal carcinoma, RCC), Ig, TCR (B, T leukemia, lymphoma, myeloma).

According to another embodiment, the antigen is a protective antigen. Protective antigens are specifically targeted by the acquired immune response of the host and able to induce protection in the host against infectious and non-infectious diseases. Examples of protective antigens for different diseases—without limitation—are: Lef; LF; PA; PA63; PA63-LAMP1; PA83; Pag; PagA; TPA-PA63; TPA-PA63-LAMP1; UQ-PA63; BoNT/A; BoNT/A1; BoNT/B; BoNT/C(Hc50); BotA; FHc; Fragment C from *Clostridium tetani*; TTC; Tetanus toxoid; Tox; Diphteria toxoid; spaA; Hly; p60; Ag85B; Ag85A; Ag85A; Ag85B; Apa; bfrA; DnaK; ESAT-6; EsxA (ESAT-6); EsxB; FbpA (Ag85A); FbpB; FbpD; HBHA; KatG; Mpt63; MPT64; MPT83; Mtb72F; PE20; PepA; PPE14; PPE18; PPE31; PstS1; PstS3; Rv1806; Rv1807; Rv2660c; ClfA; can; efb; FnbA; isdB; MecA; BipA; BPS; Rib; Sip; binding protein Eag; collagen binding, ancillary pilus subunit Cne; Fbp; Fnz; HAP; Sfs; CbpA; ClpP; GltX; Gnd; Lp1A; phpA-79; PiaA; Ply; PsaA; PspA; psrP; SrtA; emm1; FbaA; FBP54; Sfb; Sib35; APP7_1016; ApxIA; apxIA; ApxIIA; apxIIA; CP; Lipopolysaccharide; AroA; AsaP1; brkA; Cpn60; CyaA; FhaB; Prn; PtxA; PtxB; PtxC; PtxD; PtxE; S1; DbpA; OspA; OspB; OspC; AsnC; L7/L12; P39; BAB1_0278; BCSP31; Bfr; Bp26; cob; DnaK; Gap; IalB; L7/L12; Omp16; Omp19; Omp25; Omp31; ORF; P39; Rp1L; SodC; SurA; Tig; FliC; LolC/E; LPS; PotF; CadF; CjaA from *C. jejuni*; CjaA from *C. jejuni* RM 1221; FlaA from *C. jejuni* 81-176; FlaA from *C. jejuni* NCTC 11168; FlaC; FspA1; FspA2; Peb1A; PorA; MOMP; PmpE/F-2; PmpG-1; Rp1F; Tarp; TC0439 adherence factor; TC0512 outer membrane protein, putative; TC0757 hypothetical protein; TC0767 hypothetical protein; TC0768 hypothetical protein; ompA; CAB049 putative penicillin-binding protein; CAB613 putative peptidase; DnaK; DnaX; GatA; GatB; GatC; Om1A; Omp1; Pomp90A; CopN; FabD; HSP-60; LcrE; PknD; Ssb; MOMP; OmpA; HspB; P1; esa1; et18; eta6; fliC; C0393; C3389; C4424; CS1; Eae; ECSE_P3-0034; EltB; FimH; FyuA; Hma; IreA; IroN; Iss; IutA; StxB2; Tir; FopA; FopB; GroEL; Ig1C1; Ig1C2; LpnA; LPS; TUL4; Wbt1; D15; Hap; Hpd; HtrA; NucA; Omp26; OmpP1; OmpP2; OmpP5; P145; P4; Pal; Tbp2; gapA; Catalase; GltA; Hsp60; HspA; HspB; NAP; oipA; UreB; VacA; ligB; ompL1; TM-1; P97; ExbB; GNA1030; GNA1162; GNA1220; GNA1870; GNA1946; GNA2001; GNA2091; GNA2132; GNA33; GNA992 (hsf); gp120; LctP; LpdA; LPS; NadA; NspA; MC58; P1; TBP2; TbpA; OmpA; ompH; ompH; OprF; OprI; PcrV; pilA; OmpA; OmpB; SpaP; DnaJ; GroEL; Hs1U; IroN; SopB; TviB; GuaB; IpaB; IpaC; IpaD; Spa32; GlpQ; TmpB; Tp92; OmpU; CtxB; TcpA; TcpF; LcrV; Caf1; HpmB; HtpG; Irp7; LcrV; Lo1A; Pla; Psn; V antigen; YapF; YdeN; YerA; YopD; YopE; YopH; YopO; YPMT1.84 (F1 capsule antigen); YP00420; YP00612; YscF; pYV0055; Fusion protein (NCBI protein GI 6018112); G from BRSV; gB; gIV; UL44; UL49; US6; US7; Env/Rex/Tax; F gene; E2; VP1; VP2; E0; Gp55; E2; 18H6 synthetic E protein; E protein; E protein from Dengue 1; E protein from Dengue 3; E protein from Dengue 4; M protein; NS1; PrM; prM from Dengue 1; prM from Dengue 2; prM from Dengue 3; VP1; EBOV NP; GP from Reston ebolavirus; GP from Sudan ebolavirus; GP from Zaire ebolavirus; NP; SGP; VP24 from Reston ebolavirus; VP24 from Zaire ebolavirus; VP30 from Reston ebolavirus; VP30 from Zaire ebolavirus; VP35 from Reston ebolavirus; VP35 from Zaire ebolavirus; VP40 from Reston ebolavirus; VP40 from Zaire ebolavirus; ZGP; env from FeLV-A/Glasgow; Env from strain FRA; Gag; 1D; 2A; 3C; 3D; FMDV A12 genome; P1; VP1; gB; UL27; ANDVsSgp1; G1; G1 and G2; Gc; HTNVsSgp1; M Segment; N protein [Topografov virus]; PUUVsSgp1; S nucleocapsid protein from Dobrava-Belgrade virus; SNVsSgp1; G glycoprotein; HAVgp2; HBVgp2 pre-S1/pre-S2/S; Hepatitis B surface antigen; Large S protein; PreS2 middle surface protein; PreS2+S (Middle protein); S protein from Duck Hepatitis B virus; Small envelope antigen; Small S protein; p27; gB from HSV-1 KOS; ICP27 from HSV-1; ICP27 from HSV-2; UL27 from HSV-1; UL27 from HSV-2; UL44 from HSV-1; UL44 from HSV-2; US4; US5; US6; US7; US8; G glycoprotein; N nucleocapsid protein; VP1; Glycoprotein B; pp65; Env; env from clade B; env from HIV 2; env from HIV-1 isolate 037 clone 08; env from HIV-1 isolate 715; env from HIV-1 strain 96ZM651; env from HIV-1 strain 976 clone 17; env from HIV-1 strain Ba-L; env from SHIV-89.6; env from SHIV89.6P; env from SIV; Env Gp160; env MN isolate; Envelope polyprotein from HXB2; gag from clade A; Gag from HIV 1; gag from HIV 2; gag from HIV subtype B; gag from HIV-1 vector pNL4-3; gag from HXB2; gag from SHIV-89.6; Gag protein from SIV-mnd 2; gag-pol; gag-pol SIV; gp120; gp120 from MN; gp120 Indian subtype C; gp41; Nef; nef from HIV 2; pol from HIV 1; pol from SHIV-89.6; rev from HIV 1; rev from SHIV-89.6; Tat; tat from HIV 2; tat from SHIV-89.6; vif from SHIV-89.6; vpr from SHIV-89.6; vpu from SHIV-89.6; Calreticulin from humans; E6; E7; L1; L2; F protein; G protein; M membrane protein; N protein; S1; VP2; VP2-VP4-VP3; G glycoprotein; ORF; VP2; HA from influenza A virus, NA from Influenza A virus, NP from Influenza A virus (A/chicken/Henan/12/2004(H5N1)); NP from Influenza A virus, NP from Influenza B virus; Envelope protein; M protein; NS1; NS3; NS5; PreM; PrM; GPC; LASVsSgp1 nucleoprotein; LASVsSgp2 glycoprotein; NP; GP; GP from Lake Victoria marburgvirus Musoke; GP from Zaire ebolavirus; NP; NP from Lake Victoria marburgvirus; NP from Zaire ebolavirus; NP Marburgvirus—Ravn; SGP; VP35; MDV040; MDV095; F fusion protein; H hemagglutinin protein; M matrix protein; N nucleocapsid protein; P phosphoprotein; HN; gM; gN; F fusion protein; F protein from strain D26; HN hemagglutinin-neuraminidase; F fusion protein; G glycoprotein; VP4; ORF2; GP5 from CH-1a; GP5 from YA1; ORF7; ubiquitin; GB; GI; GII; GIII; Gp50; IE180; UL44; US6; VP60; env; gag; VP22; RVFVsMgp1 M protein; RVFVsSgp2 N protein; RPVgp5 F; RPVgp6 H; VP2; VP4; VP6; VP7; S protein; env; E2 from Sindbis virus; TBEVgp1 polyprotein; A27L; A33R; A34R; A36R; A4L; B5R; DBL; HSR; UR; ORF67; ORF68; A21L; H3L; UR from Monkeypox virus Zaire-96-I-16; 26S mRNA; C-E3-E2-E1-6K; E1 glycoprotein; E2 envelope protein; Glycoprotein; nucleocapsid; E protein; PrM; 26S; 6K; E1; E2; E (envelope glycoprotein); NS1 (non-structural protein 1); 11C5; 12D3; 21B4; RAP-1; CP15/60; CP23; gam56; Gam82; 3-1E; 3-1E; GX3262; MIC2; Rho; TA4; CEL-170/4; Gal/GalNAc lectin; GEh29; SREHP; CWP2; CP cysteine proteinase; Gp46; M2; P4; WD; A2; Beta-tubulin; BT1; F1-ATPase; GRP-78; HASPB1; Hsp70; KMP-11; MspC; NH; ORFF; P1; H1; HASPB1; LIPO-A; P36/LACK; SMT; Cpa; Cpb; Gp63; H2B; KMP-11; LACK; LmSTI1; PSA-2; SP; SW3.1; TSA; MIC10; NcDG1; NcDG2; NcMAG1; NcMIC1; NcPDI; NcSAG1; NcSRS2; ABRA; AMA-1 from (*P. berghei*; P. chabaudi; *P. falciparum* 3D7 or *P. knowlesi*); CS from *P. berghei* str. ANKA; CS from *P. falciparum*; CS from *P. yoelii* str. 17XNL; CSP from *P. knowlesi*; eba-175; EMP1; GLURP; HEP17; HSP60 from *P. yoelii*; Hsp90; Kbeta; LSA-3; MSP-1 from *P. falciparum*; MSP1 from *P. berghei*; MSP1 from *P. knowlesi*; MSP1 from *P. vivax*; MSP1 from *P. yoelii* str. 17XNL; MSP3; MSP4/5; MSP8; PF10_0155 enolase; pfCelTOS; Pvs25; RESA; SERA-5; SSP2; SSP2 from *P. knowlesi*; TRAP from *P. falciparum*; SAG1; FABP; Il12a; Paramyosin; Sj23; TPI; calpain; GPX; Sm23; SOD; Spag-1; TA17050 merozoite-piroplasm surface antigen Tams1; P67; GRA1; GRA4; hsp70; MIC13; MIC3; MICS; Rop2; ROPE; SAG1; SAG2; MAPP15; TSA; amastigote surface protein-2; ASP-2; ASP-2 from strain Tulahuen; ASP-2 from the Y strain; ASP1; CRP-10; Cruzipain; G2; Par1; protein G4; Tc00.1047053434931.10; Tc24 from *Trypanosoma cruzi*; TS; TS from strain Y; TSA-1; AMN1; ELI-Ag1; GEL1; PEP1; PLB; Pmp1; Para; TcrP; URE; Angpt1; Cd276; Cd86; Fas; Flt3; Il18; Il25; Il33; LPS lipopolysaccharide; Ph1 p 12 (*Phleum pratense*); Ph1 p I allergen [*Phleum pratense*]; Ph1 p7 protein [*Phleum pratense*]; Tbx21; Tnfrsf13b; Tnfrsf9; COL2A1; Collagen type II; hsp65 from *M. leprae*; ACPP; AFP; AFP from human; ANTXR1; Cc121a; Cd401g; Cd80; Cd86; CEA; CEACAM3; CTAG1B; CTLA4; E2A; Eng; EPCAM; ERBB2; Fap; Fas1; FASLG; Flt3; Fosl1; Fragment C from tetanus toxin; GAST; GM-CSF; gp100; gp75; GPC3; GRP; H2-K1; Heat shock protein; hsp70; HuD; IgG Fc; Il18; Immunoglobulin; KDR; KLK3; MAGE-1; MAGEA3; Mcam; MLANA; MUC1; Muc1; PAP; Pdgfrb; Pme117; Prostate specific antigen; Prostate stem cell antigen; Prostate-specific membrane antigen; PSCA; SCFV; SCGB2A2; SILV; SLC5A5; Steap1; Surface antigen from Hepatitis B; Survivin; TERT; TNFRSF18; TPBG; TRP-1; TRP-2; Trp2; Trp53; Tyrosinase; Tyrosinase from Mouse; TYRP1; Ubiquitin; VEGFA; WT1; BAX; Gad65; IgG Fc; MBP from guinea pig; Mog; IRBP from humans; Ricin A chain.

According to another embodiment, the antigen comprises antigenic material derived from heat-killed/formalin killed whole organisms or extracts of organisms causing diseases such as the ones listed above without limitation.

Additionally, the present invention provides experimental data showing that the Ecotin polypeptide is a good antigen against *Salmonella* infection in mice.

It is apparent to someone who is skilled in the art that this invention will be useful for any specific antigen where a specific neutralizing antibody response or specific cellular immune response would be useful for eliminating the physiological or disease state associated with that antigen.

BRIEF DESCRIPTION OF THE DRAWINGS

FIG. 1 depicts a circle map of a pET-22b(+) Vector (Novagen) used in Example 1 to obtain the final expression vectors. The pET-22b(+) vector carries an N-terminal pelB signal sequence for potential periplasmic localization, plus optional C-terminal His•Tag® sequence. Unique sites are shown on the circle map. The sequence is numbered by the pBR322 convention, so the T7 expression region is reversed on the circular map.

FIGS. 2A-2B show a picture of a SDS-PAGE (2A) wherein purified polypeptides were stained with Coomassie Blue; and a Western Blot (2B) where a monoclonal antibody anti-His-Tag was used to determine the identity of the proteins. Lanes correspond to: M: molecular weight markers, 1: modified Ecotin, 2: modified Aprin, 3: modified Staphostatin A, 4: modified Staphostatin B and 5: modified Y Inhibitor.

FIGS. 3A-3B show the production of pro-inflammatory cytokines in culture supernatants of dendritic cells (DCs). Bone marrow derived DCs from BALB/c mice were incubated with OVA alone or OVA plus different concentrations of each polypeptide of Table 1 (1, 10 or 50 μg/ml) and the production of pro-inflammatory cytokines in culture supernatants was evaluated by ELISA. Production of IL-6 (3A) and TNF-α (3B) is shown in pg/ml.

FIG. 4 illustrates the production of pro-inflammatory cytokines in culture supernatants of BMDCs. BMDCs from C3H/HeJ mice were incubated with different concentrations of each polypeptide of Table 1 (25, 50 or 100 μg/ml) and the production of pro-inflammatory cytokines in culture supernatants was evaluated by ELISA. Production of IL-6 is shown in pg/ml.

FIGS. 5A-5B show the production of pro-inflammatory cytokines in culture supernatants of dendritic cells (DCs). Bone marrow-derived DCs from C57BL/6 mice were incubated with different concentrations of each polypeptide of Table 1 (10, 50 o 100 µg/ml) and the production of pro-inflammatory cytokines in culture supernatants was evaluated by ELISA. Production of TNF-α (5A) and IL-6 (5B) is shown in pg/ml.

Figure 6:
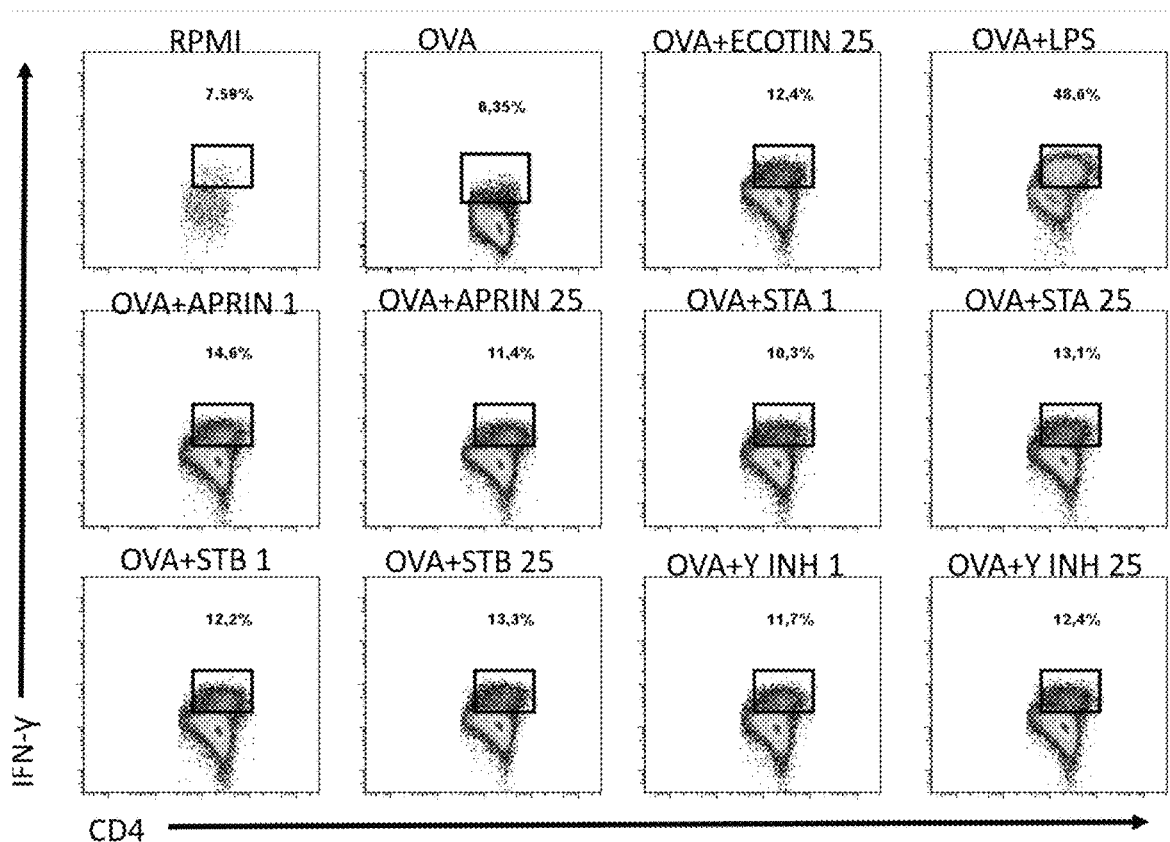
Figure 7A:
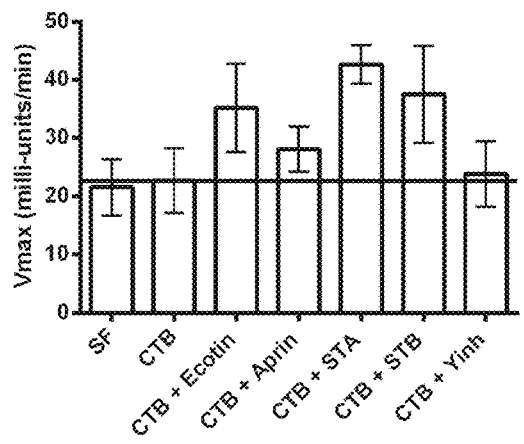
Figure 7B:
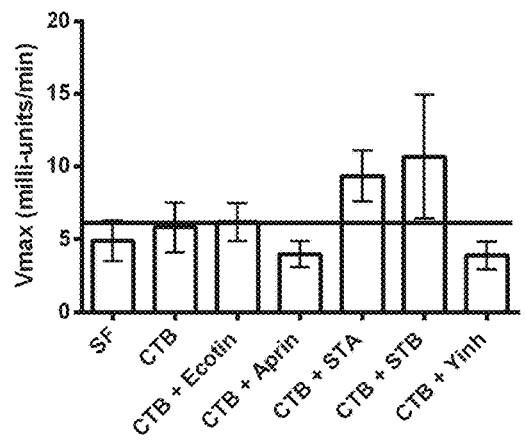
Figure 7C:
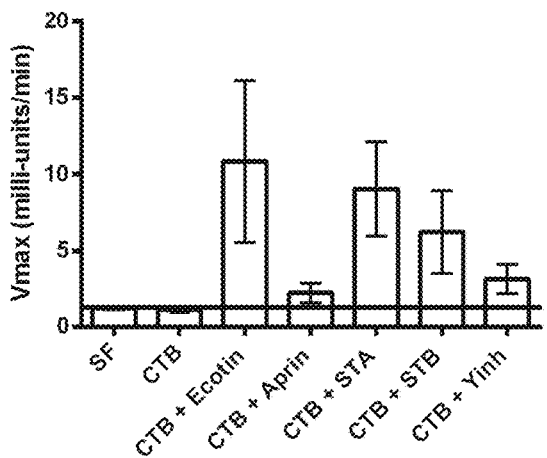
Figure 7D:
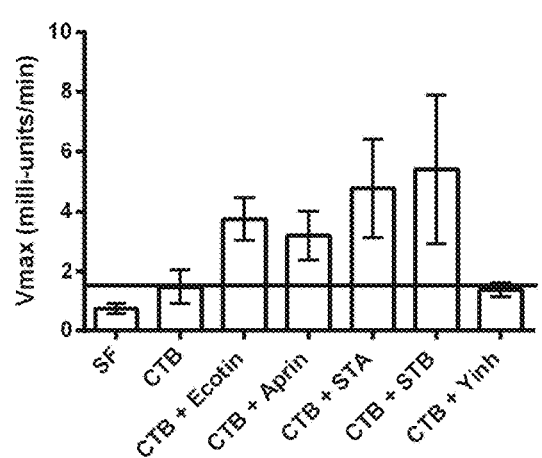
Figure 8A:
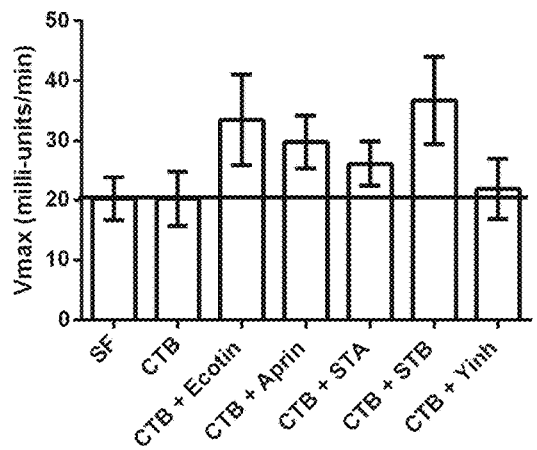
Figure 8B:
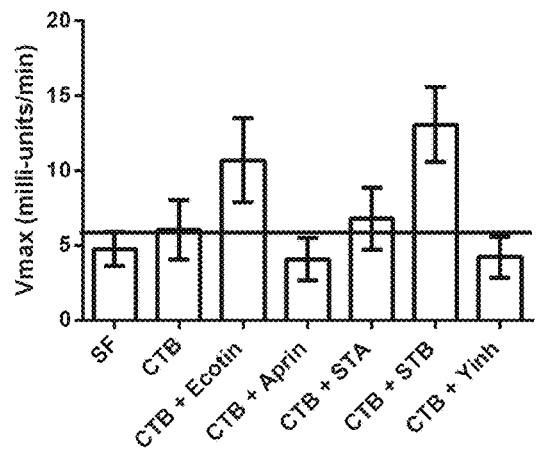
Figure 8C:
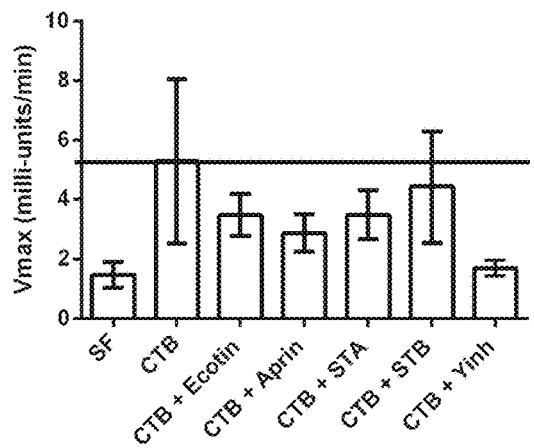
Figure 8D:
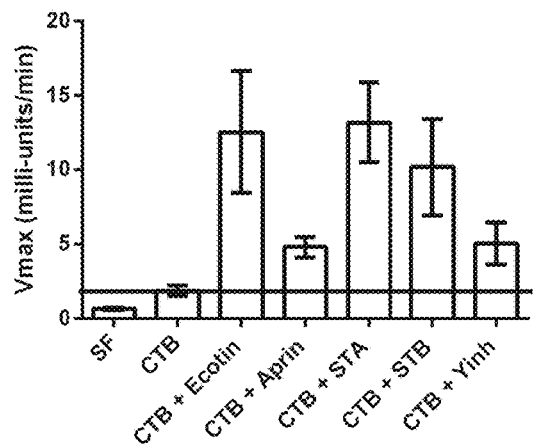

FIG. 6 shows the production of IFN-γ by specific CD4+ T cells, measured by flow cytometry. BMDCs from BALB/c mice were incubated with medium (RPMI), OVA alone or OVA plus different concentrations of each polypeptide of Table 1, then washed and co-cultured with splenocytes from DO11.10 transgenic mice. Cells were treated with brefeldin A. Afterward cells were harvested and stained with specific antibodies anti-CD4, fixed, permeabilized and stained intracellularly with anti-IFN-γ Ab. Results are expressed as percentage of CD4+ T cell producing IFN-γ.

FIGS. 7A-7D show Ag-specific antibody responses induced after oral co-administration of modified Ecotin, Aprin, Staphostatin A or Staphostatin B polypeptides with CTB as Ag. BALB/c mice were immunized on days 0, 7 and 14. Specific antibody responses (anti-CT IgA and IgG) at feces and serum were evaluated by ELISA at 7 days after second immunization. Results are expressed as Vmax (mean±SD) (mili units/min).

FIGS. 8A-8D show Ag-specific antibody responses induced after oral co-administration of modified Ecotin, Aprin, Staphostatin A or Staphostatin B polypeptides with CTB as Ag. BALB/c mice were immunized on days 0, 7 and 14. Specific antibody responses (anti-CT IgA and IgG) at feces and serum were evaluated by ELISA at 7 days after third immunization. Results are expressed as Vmax (mean±SD) (mili units/min).

Figure 9:
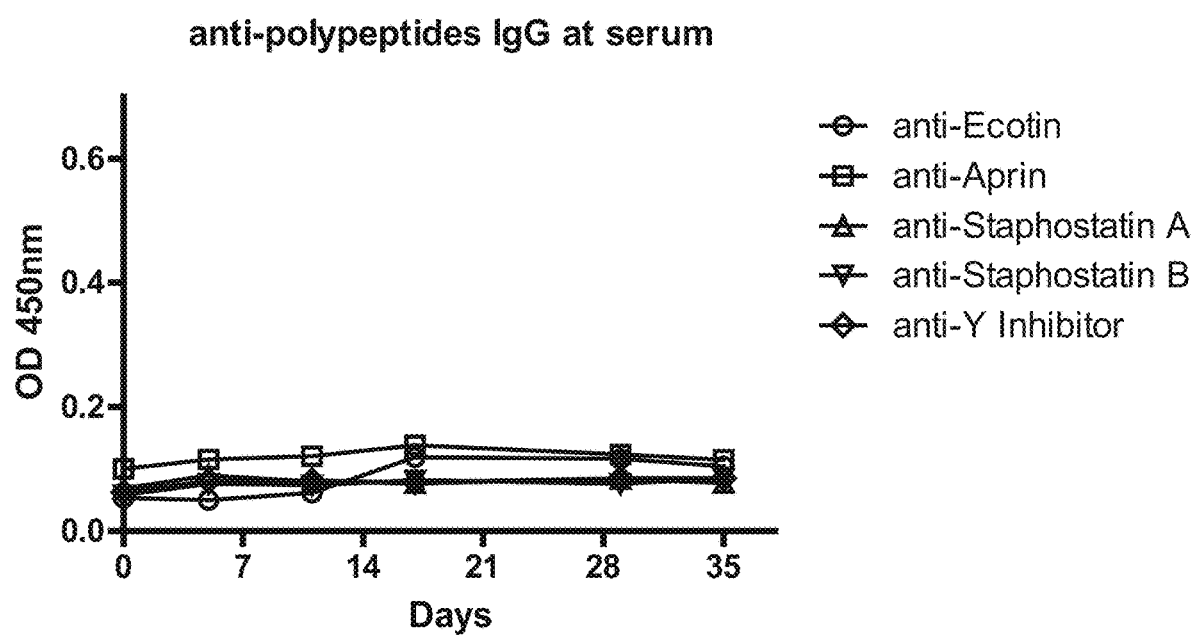

FIG. 9 shows Ag-specific antibody responses induced after oral co-administration with modified polypeptides of the invention. Specific antibody responses anti-Ecotin IgG, anti-Aprin IgG, anti-Staphostatin A IgG, anti-Staphostatin B IgG and anti-Y Inhibitor IgG were evaluated at different time points by ELISA. Results are expressed as Optical density at 450 nm.

Figure 10A:
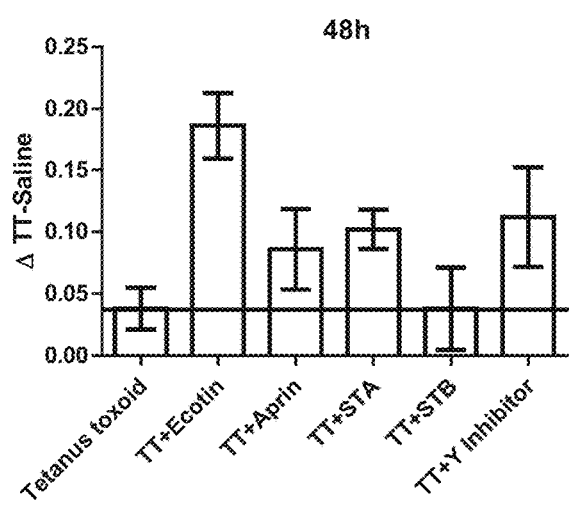
Figure 10B:
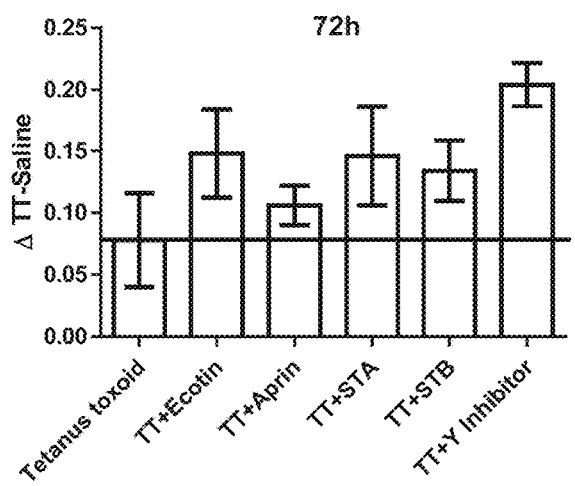

FIGS. 10A-10B show Delayed-type hypersensitivity (DTH) response to TT in mice immunized with TT plus each polypeptide of Table 1. TT was injected into one footpad, and saline was injected into the contralateral footpad, as a negative control. The thickness of both footpads was measured 48 (10A) and 72 h (10B) later and the increment between TT and saline injected was plotted.

Figure 11:
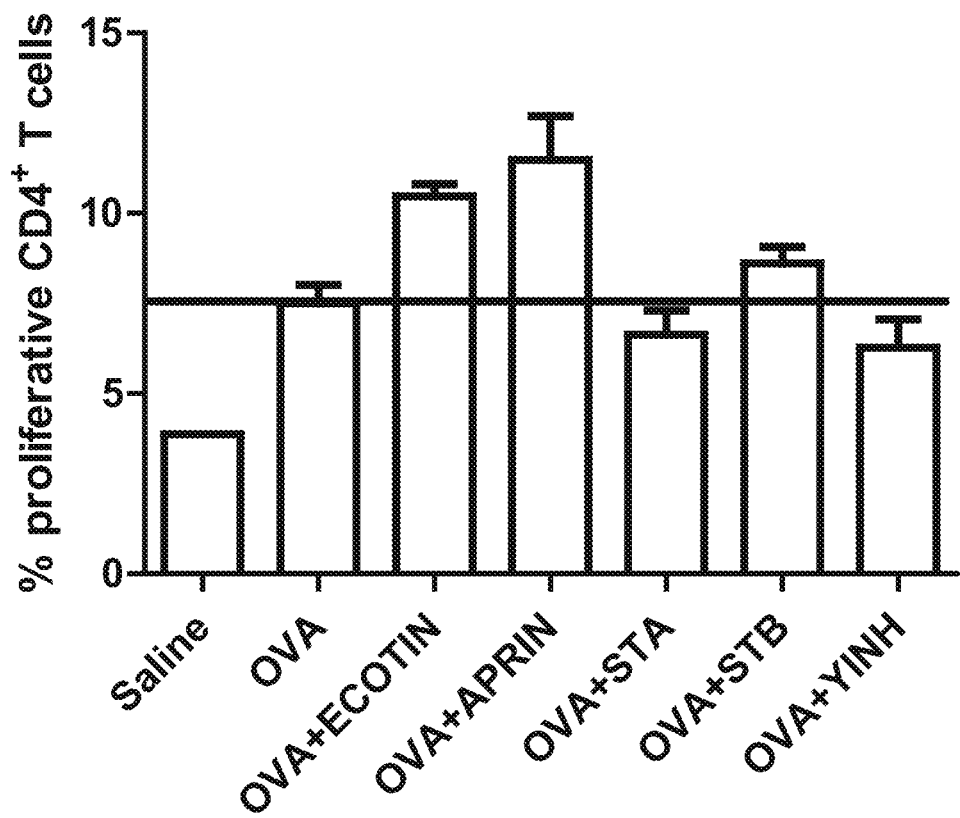

FIG. 11 shows in vivo proliferation of CD4+ T cells. CD4+ T cells from DO11.10 were labeled with CFSE and transferred to WT BALB/c mice. Mice were orally administered with saline, OVA or OVA plus each polypeptide of Table 1. Three days later spleens were obtained and cell suspensions were analyzed by flow cytometry for CFSE dilution. Data are represented as percentage of CD4+ CFSE+ proliferative T cells (mean±SD).

Figure 12:
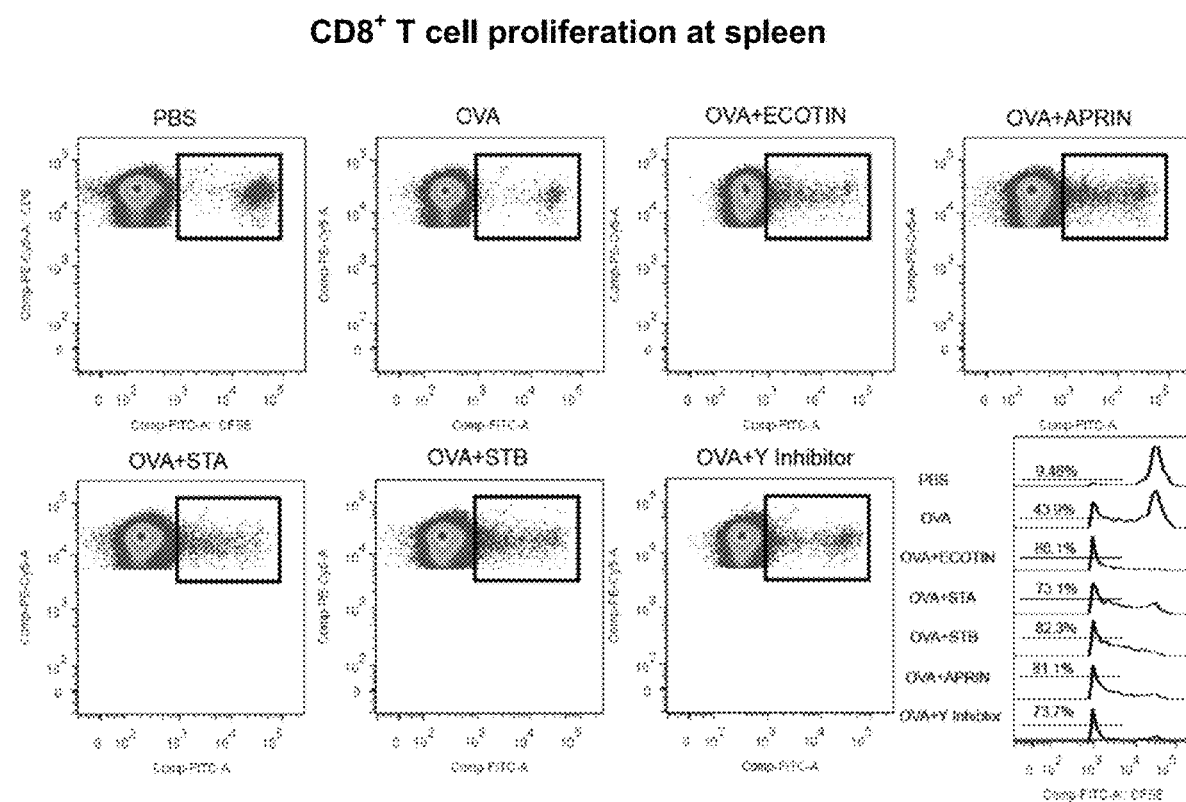
Figure 12:
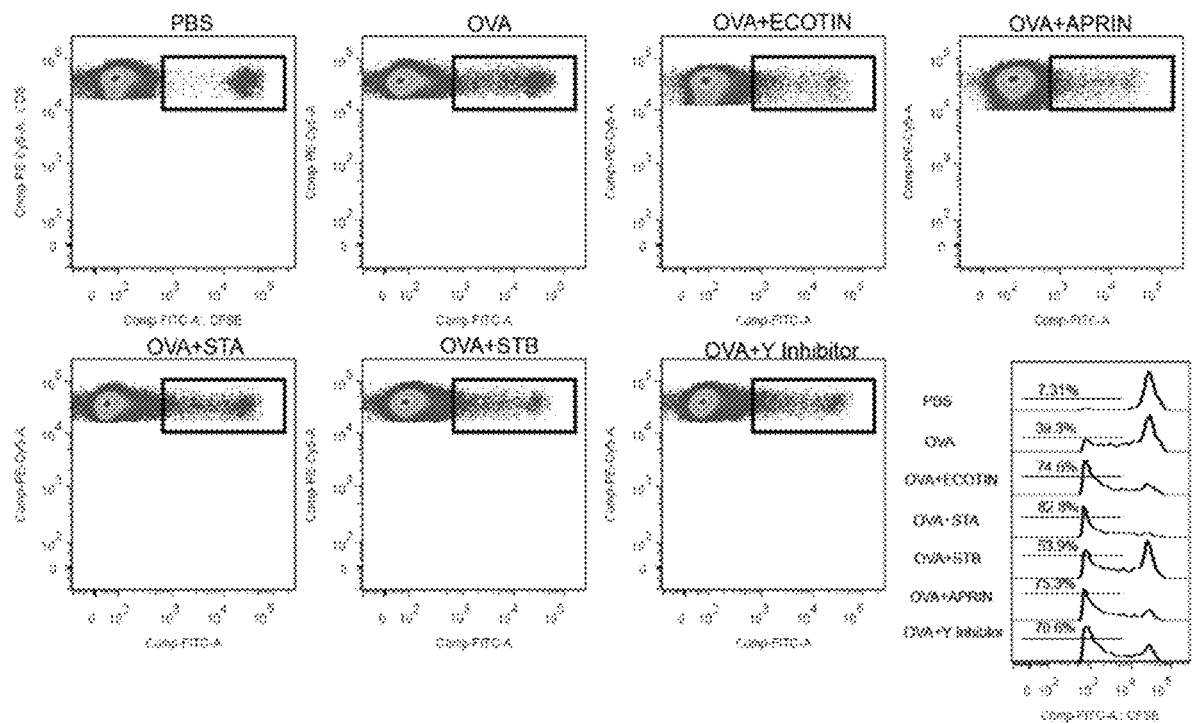
Figure 12C:
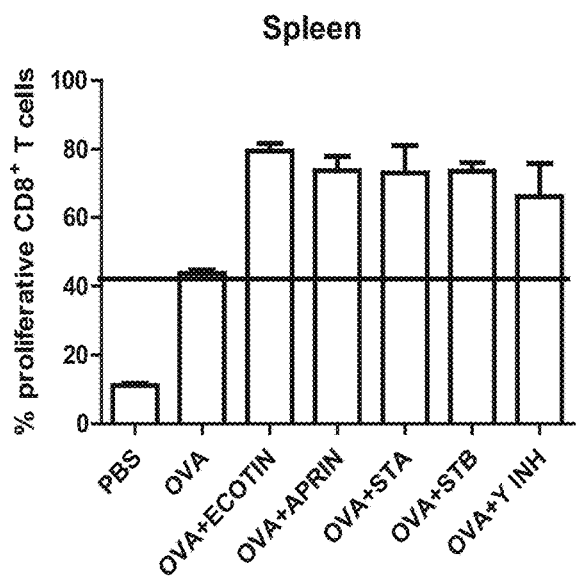
Figure 12D:
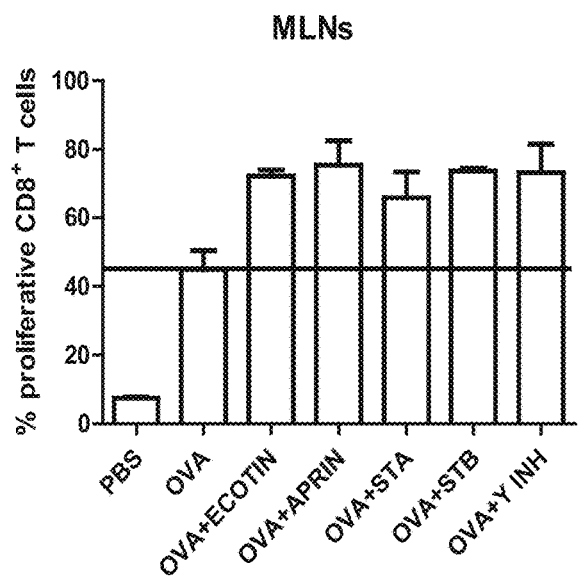

FIGS. 12A-12D illustrate in vivo proliferation of CD8+ T cells. Spleen cells from OT1 mice were labeled with CFSE and transferred to WT C57BL/6 mice. Mice were orally administered with saline, OVA or OVA plus each polypeptide of Table 1. Three days later spleens and MLNs were obtained and cell suspensions were analyzed by flow cytometry for CFSE dilution. Results are shown as dot plots and representative histograms (FIG. 12 A and FIG. 12 B) and bar graph (FIGS. 12C-12D). Data are represented as the percentage of CD8+ CFSE+ proliferative T cells.

Figure 13A:
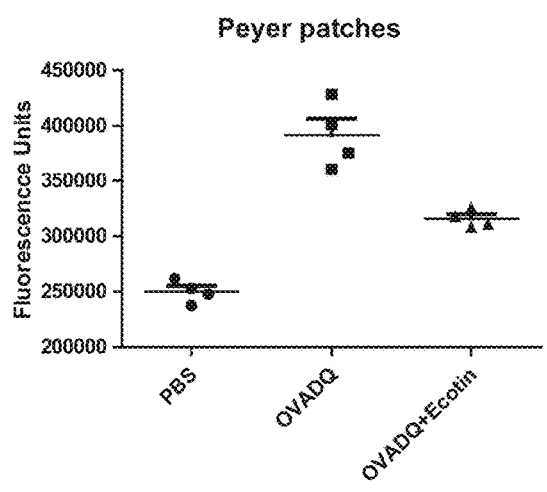
Figure 13B:
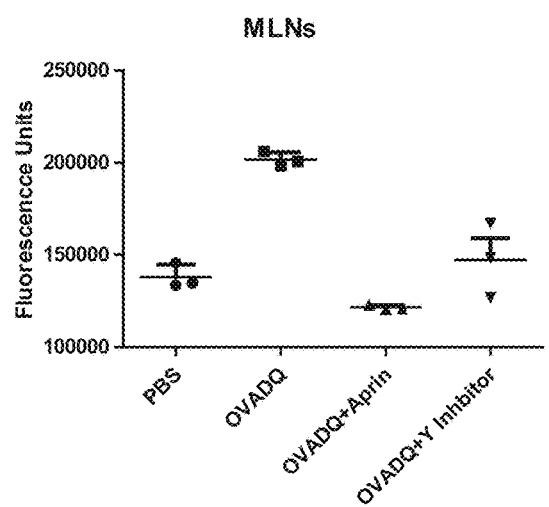

FIGS. 13A-13B illustrate reduction of Ag susceptibility to proteolysis within cells at Peyer's Patches (PPs) (13A) and Mesenteric Lymph Nodes (MLNs) (13B). Mice (n=3/group) were i.g. administered once with OVADQ plus i) buffer, ii) modified Ecotin, iii) modified Aprin, or iv) modified Y Inhibitor. Ag status was determined by detection of fluorescence in a fluorimeter. Fluorescence increase is proportional to Ag degradation. Results are expressed as mean fluorescence intensity (arbitrary units=a.u.)±SEM.

Figure 14:
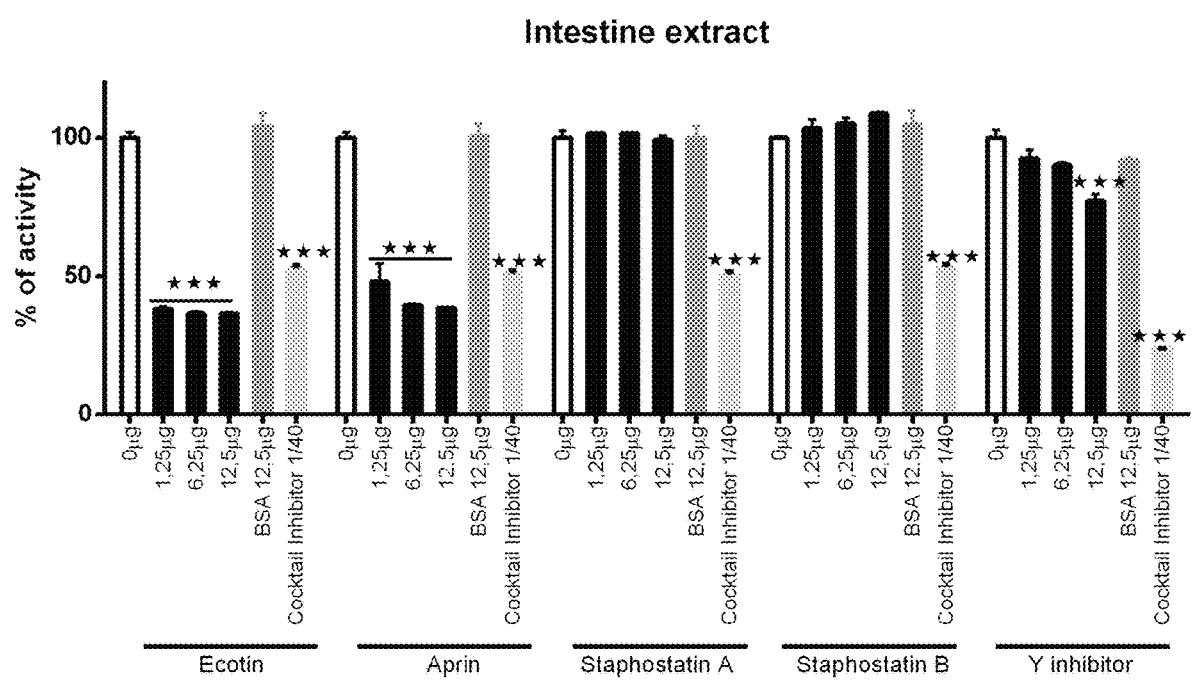

FIG. 14 illustrates protection of Ag from intestine extracts digestion by the modified Ecotin, Aprin, Staphostatin A, Staphostatin B and Y inhibitor polypeptides. Inhibitor cocktail and BSA were positive and negative controls respectively. The substrate casein BODIPY FL was added and the fluorescence intensity measured in a fluorescence plate reader. Results are shown as mean % of proteolytic activity±SEM. ***$P<0.001$ vs BSA group.

Figure 15:
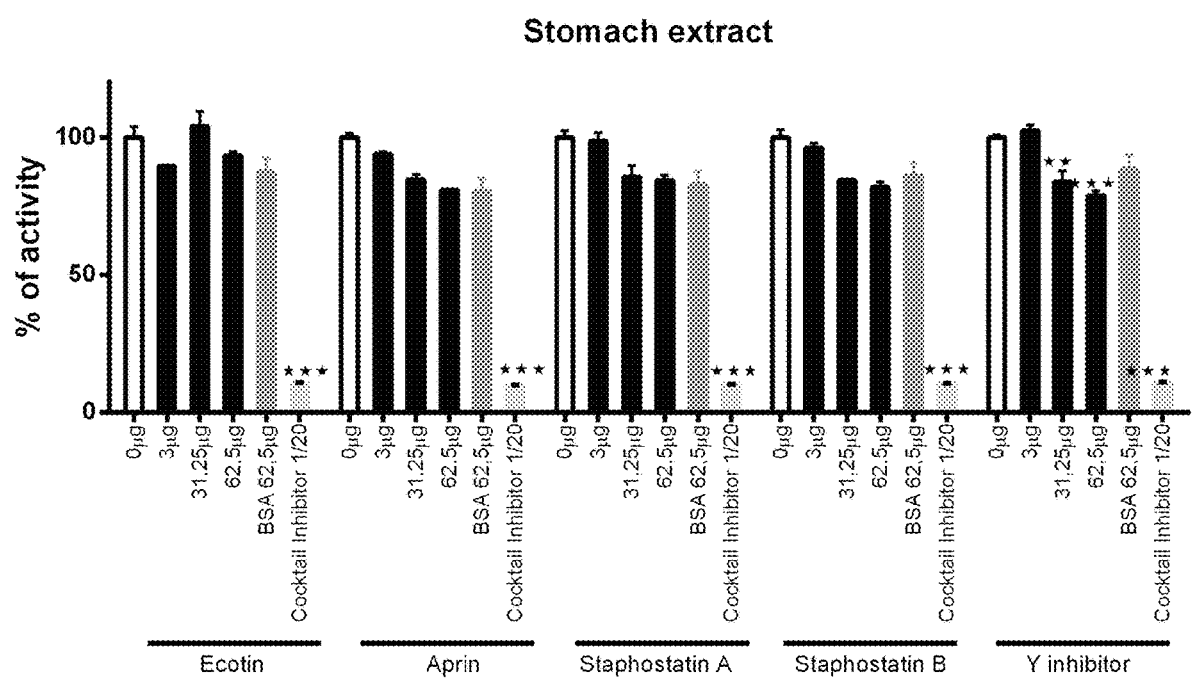

FIG. 15 illustrates protection of Ag from stomach extracts digestion by the modified Ecotin, Aprin, Staphostatin A, Staphostatin B and Y inhibitor polypeptides. Inhibitor cocktail and BSA were positive and negative controls respectively. The substrate casein BODIPY FL was added and the fluorescence intensity measured in a fluorescence plate reader. Results are shown as mean % of proteolytic activity±SEM. $P<0.01$,*$P<0.001$ vs BSA group.

Figure 16:
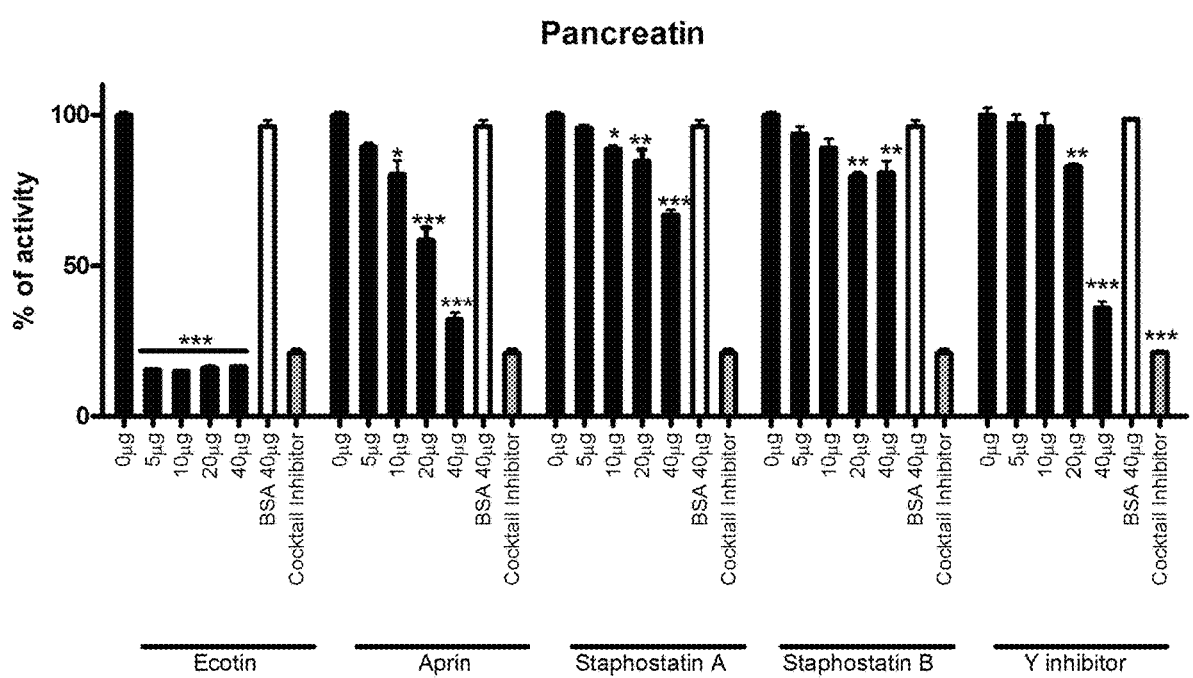

FIG. 16 illustrates protection of Ag from pancreatin digestion by the modified Ecotin, Aprin, Staphostatin A, Staphostatin B and Y inhibitor polypeptides. Inhibitor cocktail and BSA were positive and negative controls respectively. The substrate casein BODIPY FL was added and the fluorescence intensity measured in a fluorescence plate reader. Results are shown as mean % of proteolytic activity±SEM. *$P<0.05$, $P<0.01$, *$P<0.001$ vs BSA group.

FIGS. 17A-17B show protection induced by Ecotin polypeptide against *Salmonella* infection. The results are represented as amount of CFU per gram of tissue at spleen (17A) and liver (17B) of BALB/c mice immunized at days 0, 15 and 30, either intragastrically with physiologic solution (SF), Ecotin (100 µg), Ecotin (100 µg)+CT (10 µg), Ecotin (100 µg)+U-Omp19 (150 µg), or intraperitoneally with Ecotin (20 µg) plus Freund Incomplete adjuvant-FIA-(100 µL).

DETAILED DESCRIPTION OF THE INVENTION

The present application discloses modified polypeptides which show immunomodulating and immunostimulating properties. Said modified polypeptides are recombinant polypeptides of bacterial origin.

As used herein, the terms "immunomodulating", "immunomodulation" refer to agents that alter the immune response by suppression (immunosuppressive) or enhancement (immunostimulant). An immunomodulator may be defined as any biological or synthetic substance that can stimulate/suppress either innate or adaptive or both arms of the immune system.

The present inventors have shown that the modified polypeptides of the invention can induce the activation of Dendritic Cells (DCs). Thus, according to a particular embodiment, the polypeptides of the invention are formulated in pharmaceutical compositions for modulating immune responses.

According to another embodiment the modified polypeptides of the invention are the adjuvant components of a pharmaceutical composition for eliciting an immune response against the specific antigen present in the pharmaceutical composition.

As used herein, the term "adjuvant" refers to substances that, incorporated to the antigen (Ag) or simultaneously administered with it, induce a more effective immune response against the antigen. They may be used to enhance the immune response against an Ag in several ways: they can enhance the magnitude of the immune response against a weak Ag; increase the rate and duration of the immune response, modulate antibody (Ab) avidity; isotypes or subclass distribution; stimulate and modulate the cellular immune response; promote the induction of local immune response (e.g., mucosa); decrease the amount of necessary Ag and reduce the vaccine cost; or they may help in avoiding Ag competence which exists in combined vaccines (21).

Adjuvant-mediated enhancement of the immune response can be assessed by any method known in the art, including without limitation one or more of the following: (i) an increase in the number of antibodies produced in response to immunization with the adjuvant/antigen combination versus those produced in response to immunization with the antigen alone; (ii) an increase in the number or activation state of T cells recognizing the antigen or the adjuvant; (iii) an increase in the level of one or more cytokines; and (iv) in vivo protection after live challenge.

An immune response is believed to be enhanced, if any measurable parameter of antigen-specific immunoreactivity (e.g., antibody titer or T cell production) is increased at least 10% when a subject is challenged with an antigen and adjuvant compared to a subject challenged with the antigen alone. In certain embodiments of the present invention, an immune response is enhanced if any measurable parameter of antigen-specific immunoreactivity is increased by at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 350%, at least 400%, at least 450%, at least 500%, or at least 1000%.

A non-specifically immune response is believed to be enhanced, if any measurable parameter of immunoreactivity (e.g. cytokine production) is increased by at least 10% in a subject who is administered a polypeptide of the invention without administering an antigen. In certain embodiments of the present invention, an immune response is enhanced if any measurable parameter of immunoreactivity is increased by at least at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 350%, at least 400%, at least 450%, at least 500%, or at least 1000%, in a subject who is administered a polypeptide of the invention without administering an antigen.

The term "antigen", as used in the present invention, is a substance or molecule capable of eliciting an immune response and generating (specific) antibodies or cellular responses against it.

As used herein, an "immunogen" is an antigen or any substance that may be specifically recognized by components of the immune system, such as antibodies or lymphocytes. Thus, an immunogen is capable of inducing an immune response, either antibodies or cellular.

Therefore, for the purposes of present invention, the term "immunogen" and "antigen" have the same meaning and are defined as any substance against which, in an immunocompetent organism, antibodies or a cellular immune response may be induced. Accordingly, both terms may be used interchangeably herein, i.e., antigen is considered a synonym of immunogen in the present application.

According to a preferred embodiment, the antigen is selected from the group of pathogen-derived antigens, tumor cell antigens, self-antigens and allergens. Pathogen-derived antigens may be from bacteria, virus, parasites or fungi.

According to a preferred embodiment, the pathogen-derived antigen is selected from the group of viral antigens, bacterial antigens, parasitic antigens or fungal antigens.

As used herein, a self-antigen is an endogenous antigen that is recognized as non-self, but to which the healthy immune system of the parent organism is tolerant.

As used herein, an allergen is a type of antigen capable of inducing an allergy.

In additional embodiments, the invention relates to a vaccine composition comprising a) one or more polypeptides described herein, b) an antigen, and c) a pharmaceutically acceptable carrier or diluent, wherein the amounts of a) and b) in combination are effective to elicit an immune response.

A vaccine is any pharmaceutically acceptable preparation used as preventive or therapeutic administration to confer immunity against a specific disease.

As used herein, a "vaccine composition" is a biological preparation that provides active acquired immunity to a particular disease. In other words, a vaccine can be used to elicit protective immunity in a recipient. Thus, after a subject has been vaccinated with an antigen, a vaccine prevents, delays, or lessens the severity of the development of a disease in the subject exposed to the same or a related antigen in relation to a non-vaccinated subject. Protective immunity provided by a vaccine can be humoral (antibody-mediated) immunity or cellular immunity, or both. Vaccination may, e.g., eliminate or reduce the load of a pathogen or infected cells, or produce any other measurable alleviation of an infection. Vaccination may also reduce a tumor burden in an immunized (vaccinated) subject.

A vaccine typically contains an agent that resembles a disease-causing organism, and is often made from killed or weakened disease-causing organisms (or crucial fragments, products or derivatives). Typically, a vaccine is a suspension containing live, attenuated, modified, or killed organisms (or their toxins), or tumor antigens, which upon administration into the body stimulates the immune system to produce antigen-specific immune responses, antibodies and/or cellular immune mechanisms.

In a further aspect, the present invention relates to a nucleic acid sequence encoding a polypeptide of the invention. The term "nucleic acid" is well known to the skilled person and encompasses DNA (such as cDNA) and RNA (such as mRNA). The nucleic acid can be either double stranded or single stranded, linear or circular. Said nucleic acid molecule is preferably comprised in a vector which is preferably comprised in a host cell. Said host cell is, e.g. after transformation or transfection with the nucleic acid sequence of the invention, capable of expressing the polypeptides. For that purpose, the nucleic acid molecule is operatively linked with control sequences.

In a further aspect, the present invention relates to vectors. A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multiple cloning site and a selectable marker. The vector itself is generally a nucleotide sequence, commonly a DNA sequence that comprises an insert (transgene) and a larger sequence that serves as the "backbone" of the vector.

Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences such as a promoter sequence that drives expression of the transgene. Insertion of a vector into the target cell is usually called "transformation" for bacterial cells, "transfection" for eukaryotic cells, although insertion of a viral vector is also called "transduction".

In the present invention, sequences were digested with NdeI and XhoI restriction enzymes and cloned into pET22b (+) vector (Novagen) to obtain the final expression vectors. Obtained vectors were used to transform E. coli BL21 (DE3) competent cells (Novagen; Genotype: F-ompT hsdSB (rB-mB-) gal dcm (DE3)).

Other plasmids may also be used for introducing the nucleotide sequences of interest into the expression vectors, such as, for example: Pet-12a, pET-20b(+), etc. Also, other expression systems may be used for the expression of the polypeptides, such as, prokaryotic or eukaryotic protein expression systems (i.e. bacteria, yeast, plant-, insect- or mammalian-cells systems) even cell-free systems (i.e E. coli extracts, germ wheat extracts). Additionally, depending on the selected expression system and the final formulation sequences may be cloned in other vectors for each expression system.

As used herein, the term "host cell" is intended to refer to a cell into which a nucleic acid encoding a polypeptide of the invention is introduced by transformation, transfection and the like. It should be understood that such terms refer not only to the particular subject cell but to the progeny or potential progeny of such cell. Because certain modifications may occur in succeeding generations due to either mutation or environmental influences, such progeny may not, in fact, be identical to the parent cell, but are still included within the scope of the term as used herein.

The terms "host cell," "target cell" or "recipient cell" are intended to include any individual cell or cell culture that can be or has/have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, macaque or human.

Suitable host cells include prokaryotes and eukaryotic host cells including yeasts, fungi, insect cells and mammalian cells. Preferably, the host cell is the BL21 DE3 strain from E. coli. These cells are chemically competent E. coli cells suitable for transformation and protein expression obtained from Novagen.

In an alternative embodiment, compositions are provided comprising a polypeptide of the invention, or produced according to the process of the invention.

The particularly preferred pharmaceutical composition of this invention comprises one or more polypeptides of the invention. Preferably, the pharmaceutical composition comprises suitable excipients or vehicles. In a preferred embodiment, the pharmaceutical composition comprises a composition for oral administration.

According to another embodiment a composition for inducing an immune response to any antigen is provided, the composition comprising one or more polypeptides of the invention or produced according to the process of the invention. Preferably, the composition is a pharmaceutical composition.

As used herein, the term "pharmaceutical composition" relates to a composition for administration to a subject.

Subject, as used herein, "a subject" means any animal subject, including mammalian subjects, such as humans and domestic mammals.

As disclosed herein, the polypeptides of the invention may be administered in conjunction with any biologically relevant antigen, such that an increased immune response to said antigen is achieved. In a preferred embodiment, the modified polypeptides of the invention and the chosen antigen are administered simultaneously in a pharmaceutical composition comprising an effective amount of the polypeptide and an effective amount of the chosen antigen. The mode of administration is preferably oral. The respective amounts of polypeptide and antigen will vary depending upon the identity of the antigen employed and the species of animal to be immunized. Thus, the vaccine preparation compositions of the present invention may be prepared by mixing the above mentioned antigens with the claimed polypeptides at a desired ratio. The preparation should be conducted strictly aseptically, and each component should also be aseptic. Naturally, any pyrogens or allergens should be removed as completely as possible.

In some embodiments, the compositions of the present invention comprise one or more pharmaceutically acceptable carriers or excipients. Excipients include any component that does not itself induce the production of antibodies and is not harmful to the subject receiving the composition. Suitable excipients are typically large, slowly metabolized macromolecules such as proteins, saccharides, polylactic acids, polyglycolic acids, polymeric amino acids, amino acid copolymers, sucrose, trehalose, lactose and lipid aggregates (such as oil droplets or liposomes). Suitable pharmaceutical carriers are well known to those of ordinary skill in the art, including, but not limited to, diluents, such as water, saline, glycerol, and others. Suitably, sterile pyrogen-free, phosphate buffered physiologic saline is a pharmaceutical carrier. Additionally, additives, such as wetting or emulsifying agents, pH buffering substances, and the like, may be present. Vaccines of the present technology are formulated into suitable dosage for the subject to which it is to be administered. The dosage administered may vary with the condition, sex, weight and age of the individual; the route of administration; and the antigen used. The vaccine may be used in dosage forms such as suspensions or liquid solutions. The vaccine may be formulated with a pharmaceutically acceptable carrier as described above.

Vaccines of the present invention may be in an aqueous form, for example, but not limited to, solutions, particles or suspensions. The vaccine can be an oil and water emulsion, such as an oil-in-water emulsion or a water-in-oil emulsion. Liquid formulations allow the compositions to be prepackaged and administered direct from their packaged form without the need for reconstitution. Compositions may be presented in vials.

The compositions of the present invention can be combined with either a liquid or solid pharmaceutical carrier, and the compositions can be in the form of tablets, capsules, powders, granules, suspensions, syrups, solutions, particularly water solutions. The compositions can also contain suitable preservatives, coloring and flavoring agents, or agents that produce slow release. Potential carriers that can be used in the preparation of the pharmaceutical compositions of this invention include, but are not limited to, gelatin capsules, sugars, cellulose derivations such as sodium carboxymethyl cellulose, gelatin, talc, magnesium stearate, vegetable oil such as peanut oil, etc., glycerin, sorbitol, agar and water. Carriers may also serve as a binder to facilitate tableting of the compositions for convenient oral administration.

The vaccine preparation composition of this invention may be maintained in a stable storage form for ready use by lyophilization or by other means well known to those skilled in the art. For oral administration, the vaccine preparation may be reconstituted as a suspension in buffered saline, milk, or any other physiologically compatible liquid medium. The medium may be made more palatable by the addition of suitable coloring and flavoring agents as desired.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of any element, step, or ingredient not specified in the claim element. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein, any of the terms "comprising", "consisting essentially of" and "consisting of" may be replaced with either of the other two terms.

The present application is better illustrated with the following examples, which should not be construed as limiting the scope of the invention. Rather, it should be understood that modifications and equivalents to such exemplary embodiments may be suggested by those skilled in the art, upon reading the present invention, without departing from the spirit and scope of the present application and the attached claims.

Items

The invention may further be described by the following items:

1. An immunomodulating and immunostimulating polypeptide having an amino acid sequence selected from SEQ ID NO. 1, SEQ ID NO. 2, SEQ ID NO. 3, SEQ ID NO. 4 and SEQ ID NO. 5.

2. A polypeptide according to item 1, wherein the amino acid sequence is SEQ ID NO. 1.

3. A polypeptide according to item 1, wherein the amino acid sequence is SEQ ID NO. 2.

4. A polypeptide according to item 1, wherein the amino acid sequence is SEQ ID NO. 3.

5. A polypeptide according to item 1, wherein the amino acid sequence is SEQ ID NO. 4.

6. A polypeptide according to item 1, wherein the amino acid sequence is SEQ ID NO. 5.

7. A pharmaceutical composition comprising (i) a polypeptide according to any one of items 1-6, and optionally (ii) a pharmaceutically acceptable excipient.

8. A pharmaceutical composition comprising (i) a polypeptide according to any one of items 1-6, (ii) one or more antigens and optionally (iii) a pharmaceutically acceptable excipient.

9. The pharmaceutical composition according to item 8, wherein the antigen is selected from viral, bacterial, fungal, parasitic tumor-derived antigens, self-antigens and allergens.

10. The pharmaceutical composition according to any one of items 7 to 9, in the form of an oral composition.

11. The pharmaceutical composition according to any one of items 7 to 9, in the form of a parenteral composition.

12. A vaccine comprising (i) a polypeptide according to any one of items 1-6, (ii) an antigen, and optionally (iii) a pharmaceutically acceptable excipient.

13. The vaccine according to item 12, wherein the antigen is selected from viral, bacterial, fungal, parasitic and tumor-derived antigens.

14. The vaccine according to any of items 12 or 13, in the form of an oral composition.

15. A nucleic acid sequence encoding a polypeptide according to any one of items 1-6, the nucleic sequence being selected from SEQ ID NO. 6 to SEQ ID NO. 10.

16. A vector comprising a nucleic acid sequence according to item 15.

17. A host cell transformed or transfected with the nucleic acid sequence as defined in item 15 or with the vector as defined in item 16, wherein the host cell is a prokaryote or a eukaryotic host cell, such as yeast, fungi, insect or mammalian cell.

18. The polypeptide as defined in any one of items 1-6, for use as an adjuvant for vaccine compositions against an antigen.

19. A polypeptide of SEQ ID NO. 1, for use as an antigen in pharmaceutical compositions.

20. The polypeptide as defined in any one of items 1-6, for use as immunomodulator in pharmaceutical compositions.

21. The polypeptide as defined in any one of items 1-6, for use as a drug-delivery agent for antigens in vaccine compositions, wherein said polypeptide is an immunomodulating and immunostimulating polypeptide that enhances a half-life of an antigen in a vaccine composition.

22. The polypeptide as defined in any one of items 1-6, for use as a drug-delivery agent in pharmaceutical compositions.

23. A method for enhancing the immune response against an antigen in a subject, comprising administering to said subject an effective amount of the pharmaceutical composition of any of items 7 to 11 or of a vaccine of any items 12 to 14.

24. A method for modulating the immune response against an antigen in a subject, comprising administering to said subject an effective amount of the pharmaceutical composition of any of items 7 to 11 or of a vaccine of any items 12 to 14.

25. A method for inducing protective immunity to an antigen in a subject, comprising administering to said subject at least one dose of an effective amount of one or more of the polypeptides of any one of items 1 to 6.

26. A method for inducing protective immunity to an antigen in a subject, comprising administering to said subject at least one dose of an effective amount of an antigen and an effective amount of one or more of the polypeptides of any one of items 1 to 6.

27. A method for inducing protective immunity in a subject, comprising administering to said subject at least one dose of an effective amount of one or more of the polypeptides of any one of items 1 to 6.

28. A method for modulating the immune response in a subject, comprising administering to said subject an effective amount of the pharmaceutical composition of any of items 7 to 11 or of a vaccine of any items 12 to 14.

29. A method for non-specifically stimulating the subject immune system comprising administering to said subject an effective amount of at least one of the polypeptides of any one of items 1 to 6 or the pharmaceutical formulations of any of items 7-11 or the vaccine formulations of items 12-14.

30. The method of items 26, 27, 28 or 29 wherein the method is selected from oral or injectable administration to a subject of at least one of the polypeptides of any one of items 1 to 6 or the pharmaceutical formulations of any of items 7-11 or the vaccine formulations of items 12-14.

31. The method of item 30, wherein the pharmaceutical formulations are administered in the form of tablets, suspensions, solutions, emulsions, capsules, powders, syrups, drinking water compositions, and feed compositions.

EXAMPLES

Example 1—Expression and Purification of Polypeptides

A nucleotide sequence selected from SEQ ID NO. 6 to SEQ ID NO. 10 was digested with NdeI and XhoI restriction enzymes and cloned into pET22b(+) vector (Novagen, Cat. No. 69744-3), (see FIG. 1), to obtain the final expression vectors. Obtained vectors were used to transform E. coli BL21 (DE3) competent cells (Novagen; Genotype: F-ompT hsdSB (rB-mB-) gal dcm (DE3)).

The nucleotide sequences are:

1-Modified Ecotin from Salmonella without signal peptide.
SEQ ID NO. 6
CATATGGCTAACAATGGCGATACCGCCCAGCCGCTGGAAAAAATCGCCCC

CTATCCGCAGGCGGAAAAAGGAATGAAGCGGCAAGTGATAACCCTTACCC

CTCAGCAGGATGAATCTACCCTCAAAGTGGAACTGTTGATTGGCCAAACG

CTGAATGTGGATTGTAACCAGCATCGCCTCGGCGGCACGCTGGAAACAAA

AACGCTGGAAGGCTGGGGCTATGACTATTATGTCTTTGATAACGTCACCT

CTCCGGTATCAACCATGATGGCCTGCCCTGAAGGTAAGAAAGAGCAAAAA

TTCGTCACCGCCTGGCTGGGTGAAGACGGGATGCTGCGCTACAACAGCAA

GCTGCCGATCGTGGTGTATACCCCGGCGAATGTGGACGTGAAATACCGCA

TCTGGAAAGCGGACGCTAACGTACAGAACGCCGTCGCGCGACTCGAG

2-Modified aprin from Pseudomonas aeruginosa (without signal peptide)
SEQ ID NO. 7
CATATGGCCAGCAGTCTGATTCTTCTCAGCGCTTCCGATCTCGCCGGGCA

ATGGACCCTGCAGCAGGACGAGGCGCCCGCGATCTGCCACCTGGAGCTGC

GCGACAGCGAAGTGGCGGAAGCCAGTGGCTACGACCTGGGCGGCGATACC

GCCTGCCTCACGCGCTGGCTGCCCAGCGAGCCGCGCGCCTGGAGGCCTAC

CCCGGCCGGGATCGCGCTGCTCGAACGCGGCGGCCTGACCCTGATGCTCC

TCGGTCGCCAGGGCGAGGGCGACTACCGGGTGCAGAAGGGCGACGGCGGG

CAGTTGGTGCTGCGCCGCGCGACGCCCCTCGAG

3-Modified staphostatin B from Staphylococcus aureus.
SEQ ID NO. 8
CATATGCACCACCACCACCACCACTATCAACTACAATTTATAAATTTAGT

TTACGACACAACCAAACTCACACATCTAGAACAAACCAATATCAATTTAT

TCATTGGTAATTGGAGTAATCATCAATTACAAAAATCAATTTGTATACGT

CATGGCGATGATACAAGTCACAATCAATATCATATTCTTTTTATAGATAC

GGCACATCAACGCATTAAATTTTCATCTATTGATAATGAAGAAATCATTT

ATATTCTTGATTATGATGATACACAGCATATCCTCATGCAAACGTCATCC

AAACAAGGTATTGGCACTTCGCGCCCAATCGTTTATGAGCGCTTAGTATA

ACTCGAG

4-Modified staphostatin A from Staphylococcus aureus.
SEQ ID NO. 9
CATATGCACCACCACCACCACCACGAACAATTTGAATTATTTAGTATTGA

TAAATTCAAATGTAATTCAGAGGCTAAGTATTATCTTAATATTATTGAGG

GAGAATGGCATCCTCAAGATTTAAATGATAGCCCTTTAAAATTTATTCTC

AGTACCTCAGACGATTCTGATTACATTTGCAAATATATAAATACAGAACA

CAAACAACTCACATTATATAATAAAAATAATAGCTCAATTGTTATTGAAA

TATTTATACCAAATGATAATAAAATACTACTAACAATTATGAACATAGAA

GCTTTAGGAACTTCTCCTAGAATGACTTTCATTAAGCATAAAAGTTAACT

CGAG

5-Modified serine carboxypeptidase Y inhibitor from Helicobacter pylori . . .
SEQ ID NO. 10
CATATGAAAACTTTTGAAGTGATGATTCAAACCGATTCAGAAGGGTATTT

GGACGCTAAATTTGGCGGTAACGCTCCTAGAGGGTTTCTCAATCCAAACG

GCTTACCCACTTATTCGCCTAAAATCTCATGGCAAAAAGTAGAAGGTGCT

CAAAGCTATGCGTTAGAACTTATTGATCATGACGCGCAAAAAGTGTGCGG

CATGTCGTTTATCCATTGGGTCGTGGGCAATATCTCTCATAATGTTTTAG

AAGAAAACGCCTCCATGATGGATAAAAGGATTACTCAAGGGGTCAATTCG

CTTACTCAAGGCTTTATCCGTTCTCCTCTTAATGAAAGCGAAAAACAACG

CTCCAATCTCAATAACAGCGTCTATATCGGCCCCATGCCTCCTAATGGCG

ATCACCATTACTTGATTCAAGTGTATGCCCTAGACATTCCTAAACTCGCC

TTAAAAGCCCCTTTTTTCTTAGGCGATTTGCATGACAAAATGCGCAACCA

-continued

```
TATCATCGCCATAGGGAGAAAGGAATTTCTATACAAGCAGTTTATGAGGA

AACTCGAG
```

According to the supplier, the pET22b(+) vector contains the following sequence landmarks:
T7 promoter 361-377
T7 transcription start 360
pelB coding sequence 224-289
Multiple cloning sites
(Nco I-Xho I) 158-225
His•Tag coding sequence 140-157
T7 terminator 26-72
lacI coding sequence 764-1843
pBR322 origin 3277
bla coding sequence 4038-4895
f1 origin 5027-5482

Figure 2A:
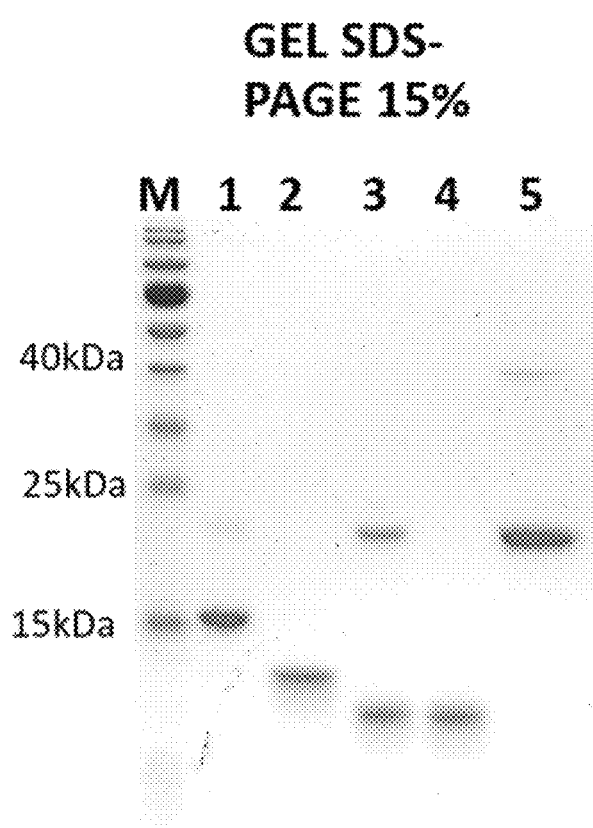
Figure 2B:
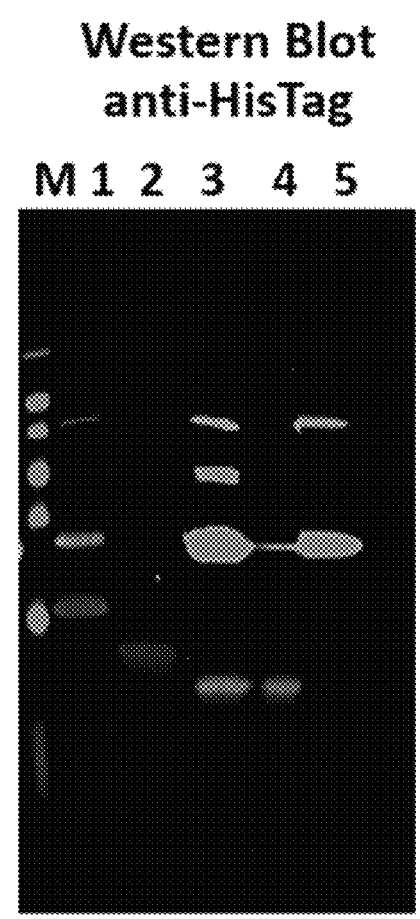

The recombinant polypeptides containing a His-Tag at the N- or C-terminus were expressed in competent E. coli (BL21 DE3) cells. Transformed cells were plated on LB+ampicillin (100 µg/ml) agar plates and incubated ON at 37° C. Then, colonies were suspended in LB plus Ampicillin (100 µg/ml) at 37° C. and shacked at 200 rpm. Optical density (OD) at 600 nm was measured and at OD 0.6-0.8 the cell culture was induced with IPTG (1 mM) during 16 h at 18° C. (180 rpm). Bacterial cell cultures were centrifuged for 10 min at 6000×g at 4° C. Pellets were stored at −20° C. Cell culture pellets were suspended in buffer pH:8 (NaH$_2$PO$_4$ 50 mM, NaCl 300 mM) sonicated on ice (3 pulses of 30 seconds) and centrifuged for 30 min at 14000×g. As the polypeptides contain a His-Tag, protein was purified by FPLC using Ni-NTA Agarose columns. Protein identity was confirmed by SDS-PAGE 15% (FIG. 2A) by Western Blot using monoclonal anti His-Tag antibody (FIG. 2B), and by mass spectrometry (not shown). LPS contamination from polypeptides was adsorbed with Sepharose-polymyxin B. Endotoxin determination was performed with Limulus amebocyte lysate (LAL) chromogenic assay. All the preparations of the polypeptides used contained <0.1 endotoxin units per mg of protein.

The amino acid sequences of the polypeptides of the invention are shown in Table 1 below.

TABLE 1

| Polypeptide | Amino acid Sequence |
|---|---|
| Modified Ecotin from Salmonella enterica without signal peptide SEQ ID NO. 1 | MANNGDTAQPLEKIAPYPQAEKGMKRQVITLT PQQDESTLKVELLIGQTLNVDCNQHRLGGTLE TKTLEGWGYDYYVFDNVTSPVSTMMACPEGKK EQKFVTAWLGEDGMLRYNSKLPIVVYTPANVD VKYRIWKADANVQNAVARLEHHHHHH |
| Modified aprin from Psuedomonas aeruginosa without signal peptide SEQ ID NO. 2 | MASSLILLSASDLAGQWTLQQDEAPAICHLEL RDSEVAEASGYDLGGDTACLTRWLPSEPRAWR PTPAGIALLERGGLTLMLLGRQGEGDYRVQKG DGGQLVLRRATPLEHHHHHH |
| Modified Staphostatin B from Staphylococcus aureus SEQ ID NO. 3 | MHHHHHHYQLQFINLVYDTTKLTHLEQTNINL FIGNWSNHQLQKSICIRHGDDTSHNQYHILFI DTAHQRIKFSSIDNEEIIYILDYDDTQHILMQ TSSKQGIGTSRPIVYERLV |
| Modified Staphstatin A from Staphylococcus aureus SEQ ID NO. 4 | MHHHHHHEQFELFSIDKFKCNSEAKYYLNIIE GEWHPQDLNDSPLKFILSTSDDSDYICKYINT EHKQLTLYNKNNSSIVIEIFIPNDNKILLTIM NIEALGTSPRMTFIKHKS |
| Modified serine carboxypeptidase Y inh. from Helicobacter pylori. SEQ ID NO. 5 | MKTFEVMIQTDSEGYLDAKFGGNAPRGFLNPN GLPTYSPKISWQKVEGAQSYALELIDHDAQKV CGMSFIHWVVGNISHNVLEENASMMDKRITQG VNSLTQGFIRSPLNESEKQRSNLNNSVYIGPM PPNGDHHYLIQVYALDIPKLALKAPFFLGDLH DKMRNHIIAIGRKEFLYKQFMRKLEHHHHHH |

Example 2—Polypeptides have Immunostimulating Properties

Figure 3A:
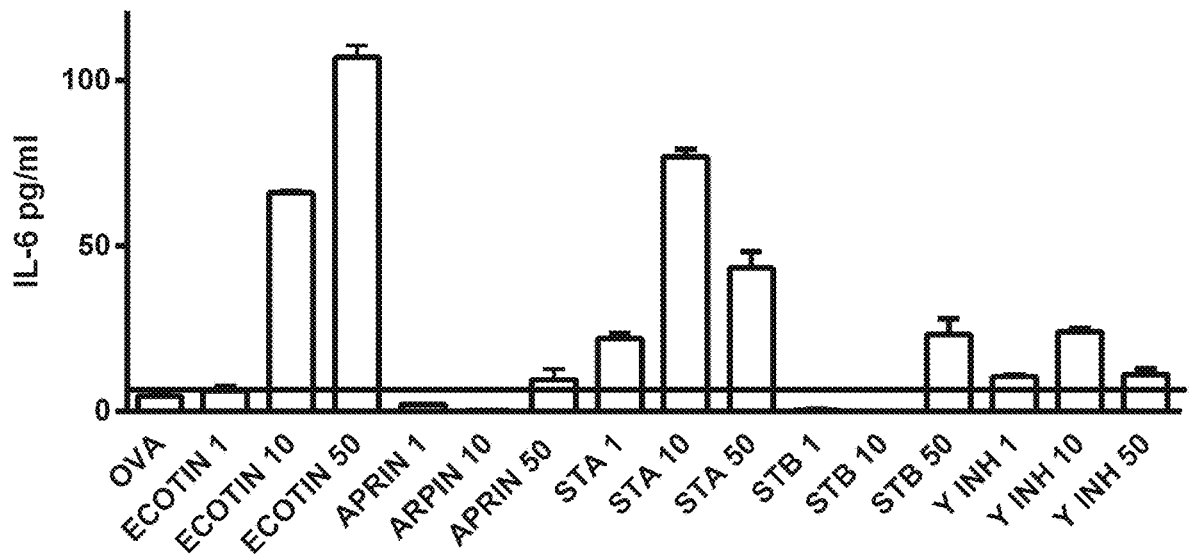
Figure 3B:
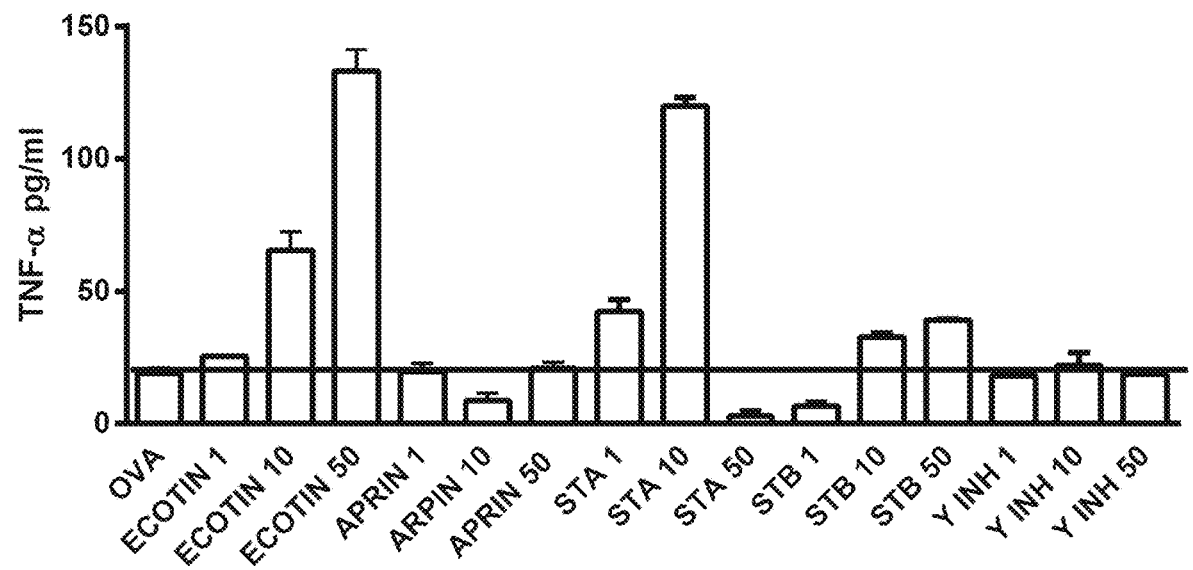

Maturation of dendritic cells (DCs) is a key step in the induction of adaptive immune responses. Thus, the ability of polypeptides of SEQ ID NO. 1-5 to induce maturation of DCs in vitro in the presence of an antigen was evaluated. Bone marrow derived dendritic cells (BMDCs) (CD11c+ MHCIIlow) from wild type BALB/c (1×10$^6$ cells/ml) were stimulated for 18 h with ovalbumin antigen (OVA, purified chicken egg OVA grade V, from Sigma) or OVA plus each polypeptide of Table 1 in different concentrations (1, 10 or 50 µg/ml) for 18 h. Then the production of pro-inflammatory cytokines in culture supernatants was determined by ELISA. DCs stimulation with OVA plus Ecotin of SEQ ID NO. 1, Staphostatin A (STA) of SEQ ID NO. 4, Staphostatin B (STB) of SEQ ID NO. 3 or Y Inhibitor (Y INH) of SEQ ID NO. 5, induced significant production of pro-inflammatory cytokines (IL-6 and TNF-α) in comparison with OVA stimulation alone (FIG. 3A and FIG. 3B). These results indicate that modified Ecotin, Staphostatin A (STA), Staphostatin B (STB) and Y Inhibitor (Y INH) polypeptides have immune-stimulatory activity on DCs.

Example 3—Polypeptides Induce Dendritic Cell Activation in C3H/Hej Mice

Figure 4:
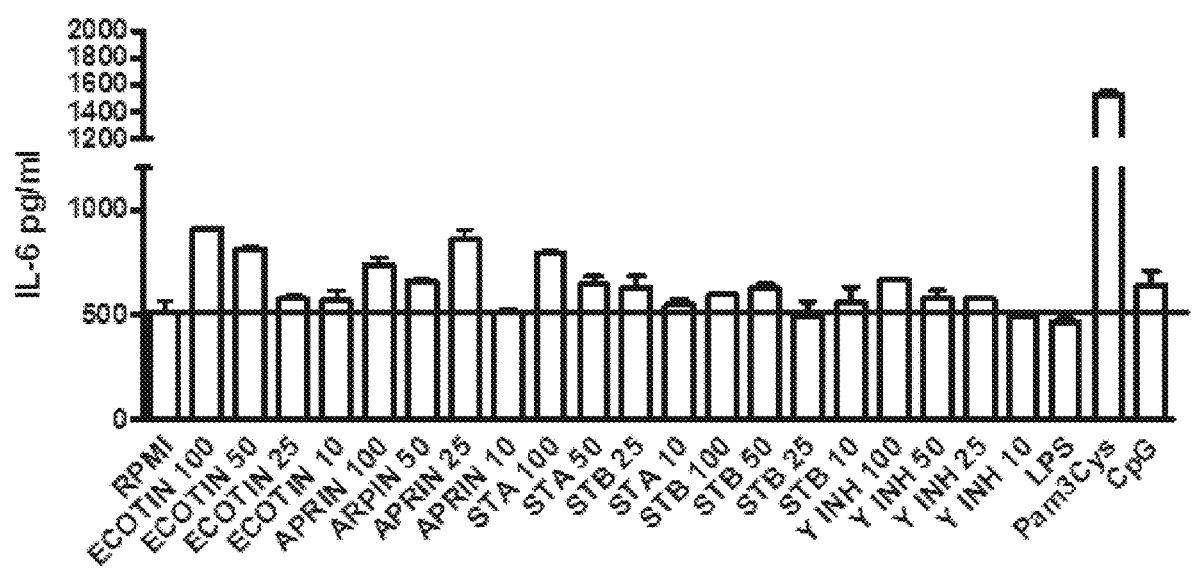

C3H/Hej mice are non-responsive to LPS (22, 23). BMDCs from C3H/HeJ mice were incubated with different concentrations of each polypeptide of SEQ ID NO. 1-5 alone in different concentrations (25, 50 or 100 µg/ml) for 18 h. Then, the production of pro-inflammatory cytokines in culture supernatants was evaluated by ELISA. Production of IL-6 is shown in pg/ml. Ecotin (SEQ ID NO. 1), Aprin (SEQ ID NO. 2) and STA (SEQ ID NO. 4) induced the production of significant levels of pro-inflammatory cytokines (IL-6) from C3H/Hej DCs (FIG. 4). These results indicate that modified Ecotin, Aprin and STA polypeptides activate DCs in a TLR4 independent manner.

Example 4—Polypeptides Induce Dendritic Cell Activation

The ability of polypeptides of the invention to induce activation/maduration of dendritic cells (DCs) in vitro was evaluated. Bone marrow-derived DCs (BMDCs) from C57BL/6 mice were incubated with different concentrations of each polypeptide of Table 1 (1, 10, or 50 µg/ml) for 18 h. Then the production of pro-inflammatory cytokines in culture supernatants was determined by ELISA. DCs stimulation with Ecotin of SEQ ID NO. 1, Aprin of SEQ ID NO. 2, Staphostatin A (STA) of SEQ ID NO. 4, Staphostatin B (STB) of SEQ ID NO. 3 or Y Inhibitor (Y INH) of SEQ ID NO. 5, induced production of pro-inflammatory cytokines TNF-α in comparison with medium alone (FIG. 5A). DCs stimulation with Ecotin of SEQ ID NO. 1 or Staphostatin A (STA) of SEQ ID NO. 4 induced production of IL-6 in comparison with medium alone (FIG. 5B). These results indicate that modified Ecotin, Aprin, Staphostatin A (STA), Staphostatin B (STB) and Y Inhibitor (Y INH) polypeptides have immunostimulatory activity on DCs Example 5—Polypeptides are Able to Induce Effector CD4+ T Cells To study if polypeptides of SEQ ID NO. 1-5 have the capacity to promote effector specific CD4+ T cells responses, D011.10 mice were used as a source of OVA-specific CD4+ T cells. Bone marrow derived dendritic cells (BMDCs) (CD11c+ MHCII low) from BALB/c mice (1×10$^6$) were pulsed with complete medium (RPMI), OVA alone, OVA plus each polypeptide or OVA plus LPS for 18 h, washed and then co-cultivated with CD4+ T cells from spleens (2×10$^6$ cells) from D011.10 transgenic mice at 37° C. for 23 h. During last 5 h cells were treated with brefeldin A. Afterward cells were harvested and stained with specific antibodies anti-CD4, fixed, permeabilized with saponin and stained intracellularly with anti-IFN-γ Ab. Production of IFN-γ by specific CD4+ T cell was measured by flow cytometry. In FIG. 6, the results are expressed as percentage of CD4+ T cell producing IFN-γ. DCs incubated with all polypeptides in two different concentrations (1 and 25 µg/ml) induced higher levels of IFN-γ production in D011.10 CD4+ T cells (ranging from 10%43% of T cell proliferation) than T cells co-cultivated with OVA alone pulsed DCs (6.35%). LPS treated BMDCs also induced a strong IFN-γ production by D011.10 cells (48.6%). These results show that Ecotin (SEQ ID NO. 1), Aprin (SEQ ID NO. 2), Staphostatin A (STA, SEQ ID NO. 4), Staphostatin B (STB, SEQ ID NO. 3) or Y Inhibitor (Y INH, SEQ ID NO. 5) promote the activation of CD4+ T cells by DCs.

Example 6—Polypeptides Induce Mucosal Immune Responses after Oral Co-Administration with an Antigen Antigen specific antibody (Ab) mucosal responses are important to achieve a protective response against many infectious diseases. To test polypeptides of SEQ ID NO. 1-5 capacity to elicit Ab responses the present inventors used, Cholera toxin subunit B (CTB) from *Vibrio cholera* and the tetanus toxoid (TT) as exemplary vaccine Ags. Presently, CTB is used in formulations of oral cholera vaccine Dukoral®, used in humanitarian's emergencies and TT in antitetanus vaccine.

Female BALB/c mice, 2 months old (n=5/group), were i.g immunized on days 0, 7 and 14 with CTB (5 µg) alone or CTB plus each polypeptide (100 µg), according to the following scheme: i) CTB, ii) CTB+Ecotin of SEQ ID NO. 1, iii) CTB+Aprin of SEQ ID NO. 2, iv) CTB+Staphostatin A of SEQ ID NO 4, v) CTB+Staphostatin B of SEQ ID NO. 3 or vi) CTB+Y Inhibitor of SEQ ID NO. 5. Other groups of BALB/c (n=5/group) mice were i.g. immunized on days 0, 7 and 14 with TT (100 µg) alone or TT plus each polypeptide (150 µg).

Feces and serum were collected 1 week after each immunization to evaluate the specific systemic and mucosal antibody responses induced. Specific antibody responses (anti-CT or anti-TT IgG and IgA) at feces and serum were evaluated at different time points by indirect ELISA.

Antibody responses were evaluated one week after the second oral dose of the Ag plus the polypeptides. At this time point, oral co-delivery of modified Ecotin, Aprin, Staphostatin A or Staphostatin B polypeptides with CTB increased anti-CT IgA in feces and serum compared with those from CTB alone immunized mice (FIGS. 7 A, 7 C). Besides, there was an increase in anti-CT IgG in feces from animals that were co-administrated with CTB plus STA or STB (FIG. 7 B), while CT-specific IgG at serum was increased in Ecotin, STA, STB or Y Inh plus CTB co-delivered mice (FIG. 7 D). One week after third immunization there was an increase in CT-specific IgA in feces from mice that were co-administered orally with CTB plus Ecotin, Aprin, STA or STB in comparison with CTB alone (FIG. 8 A). CT-specific IgG in feces increased in mice that were orally co-delivered with CTB plus Ecotin or STB (FIG. 8 B). There was an increase in CT-specific IgG in serum in those mice that were co-administered with CTB plus all the polypeptides (FIG. 8 D). Altogether, these results indicate that the addition of polypeptides of the present invention to an oral vaccine formulation increase mucosal and systemic antibody responses against co-delivered antigen.

Specific antibody responses anti-each polypeptide IgG at serum were evaluated at different time points by ELISA. In FIG. 9, anti-Ecotin IgG, anti-Aprin IgG, anti-Staphostatin A IgG, anti-Staphostatin B IgG and anti-Y Inhibitor IgG OD results are shown. Of note, Ab responses against the polypeptides were not induced. This is of importance because it was described for other adjuvants and delivery systems that antibody responses against themselves may inhibit subsequent utility. Thus, these results would support repeated use of polypeptides of the present invention contained in different vaccine formulations avoiding this problem.

Together these results indicate that co-delivery of the polypeptides of SEQ ID NO. 1-5 of the present invention with antigens increase Ag-specific mucosal as well as systemic Ab responses against co-delivered Ags.

Example 7—Polypeptides Induce In Vivo Antigen Specific Cellular Immune Responses after Oral Co-Administration with the Ag Delayed-type Hypersensitivity response (DTH) was evaluated in mice immunized with TT plus each polypeptide of SEQ ID NO. 1-5. Briefly, three weeks after the last immunization, mice were intradermally injected in one footpad with 20 µg of Ag (TT) and in the contra lateral footpad with an equal volume of saline, as a negative control. Footpad swelling was measured 48 and 72 h later using a digital caliper with a precision of 0.01 mm, and the mean increase in footpad thickness (mm) was calculated as: (footpad thickness) Ag—(footpad thickness) saline.

At 48 h there was an increase in TT-specific DTH in mice co-administered with modified Ecotin, Aprin, STA and Y Inhibitor polypeptides compared with mice immunized with TT alone (FIG. 10A), while at 72 hs all polypeptides increased TT-specific DTH (FIG. 10B). These results indicate that these polypeptides when co-delivered with an Ag, are able to induce antigen specific cellular immune responses in vivo.

Example 8—Polypeptides Induce Proliferation of Ag Specific T Cells In Vivo

Adoptive transfer assays using TCR transgenic DO11.10 or OTI mice were also performed to determine in vivo the primary antigen-specific clonal expansion of transgenic CFSE$^+$ labeled T cells following oral immunization with OVA plus the polypeptides of SEQ ID NO. 1-5.

Single-cell suspensions of spleen and lymph nodes cells from DO11.10 or OT-I mice were labeled with 5 µM CFSE. Labeled cells ($10 \times 10^6$) were injected i.v into wild type BALB/c sex-matched recipients. One day later, transferred mice received a single oral dose of saline, OVA (500 µg) or OVA plus each polypeptide (250 µg, by gavage). Three days after immunization, mice were sacrificed and spleen cells were obtained and labeled with anti-CD4 antibodies to study by flow cytometry the dilution of CFSE on transgenic CD4$^+$ T cells. Co-administration of OVA with Ecotin and Aprin showed a greater specific CD4$^+$ T cell proliferation at spleens than mice immunized with OVA alone (FIG. 11).

Other group of WT C57BL/6 mice were transferred with spleen cells from OTI mice labeled with CFSE. One day later mice were orally administered with saline, OVA (1 mg) or OVA plus each polypeptide (250 µg). Three days later spleens and MLNs were obtained and cell suspensions were analyzed by flow cytometry for CFSE dilution. Results are shown as dot plots, representative histograms (FIG. 12A and FIG. 12B) and bar graph (FIGS. 12C-12D). Data are represented as the percentage of CD8$^+$ CFSE$^+$ proliferative T cells. Co-administration of OVA plus Ecotin, Aprin, STA, STB or Y INH increased CD8$^+$ T cell proliferation at spleens (12C) and MLNs (12D) in comparison with OVA delivered alone. These results show that these polypeptides co-administered orally with the Ag enhances Ag-specific CD8$^+$ T cell responses in vivo at systemic (spleen) and mucosal sites as MLNs.

Altogether these results indicate that polypeptides increase CD4$^+$ and CD8$^+$ T cell immune responses against the co-administered Ag.

Example 9—Oral Delivery of Polypeptides Limits Proteolysis of the Co-Administered Ag within Cells from Peyer's Patches (PPs) and Mesenteric Lymph Nodes (MLNs)

To induce an adaptive immune response Ags must reach inductive sites (PPs and MLNs) of the gastrointestinal immune system. Then, it is important that the Ag could resist the harsh environment of the gut (high degradation).

OVADQ was used as an Ag, OVADQ is quenched and its hydrolysis relieves the quenching, yielding bright green fluorescent peptides. The increase in fluorescence is proportional to protein digestion. OVADQ alone, OVADQ plus each polypeptide of SEQ ID NO. 1-5 or PBS were administered i.g. to BALB/c mice (n=3/group). At 6 h post administration mice were sacrificed and PPs and MLNs were removed. Single cell suspensions were prepared, filtered through a stainless-steel sieve and washed twice in PBS solution to eliminate any extracellular Ag, thus the fluorescence determination was proportional to Ag-digestion. Total viable cells were counted using Trypan Blue. Fluorescence intensity (FI) in arbitrary units was determined in $1 \times 10^6$ cells.

Oral delivery of modified Ecotin reduced the amount of degraded Ag (OVA-DQ) that reached the Peyer patches 6 h after its co-administration (FIG. 13A). In the same way, modified Aprin and modified Y Inhibitor decreased the amount of digested OVA at the MLNs after 6 h of oral co-delivery (FIG. 13B). A reduction in the degradative status of the Ag can increase the amount of Ag that reaches these inductive sites. This would help reduce the amount of Ag needed in the formulation, thus reducing costs.

Example 10—the Polypeptides Protect Co-Administered Ag from Gut Harsh Environment The ability of polypeptides of SEQ ID NO. 1-5 to protect Ag from stomach or intestine extracts digestion was studied. Digestion of CASEIN BODIPY in presence of polypeptides was assessed using murine stomach and intestine extracts or pig pancreatic extract. Different amounts of extracts were incubated with different amounts of polypeptides for 1 h at room temperature in the appropriate buffers and then the substrate was added (CASEIN BODIPY, 1 µg/ml). Fluorescence was measured in a fluorescence plate reader and the percentage of proteolytic activity was calculated.

Intestine extracts were pre-incubated for 1 h with buffer, each polypeptide (1.25, 6.25 or 12.5 µg/ml), Inhibitor cocktail (from Sigma Aldrich, containing AEBSF 104 mM, Aprotinin 80 µM, Bestatin 4 mM, E-64 1.4 mM, Leupeptin 2 mM and Pepstatin A 1.5 mM in a ready-to-use solution in DMSO) or BSA (12.5 µg) as positive and negative controls, respectively. Then, the substrate casein BODIPY FL (1 µg/ml) was added and the fluorescence intensity measured in a fluorescence plate reader. Results are shown in FIG. 14 as mean % of proteolytic activity±SEM. ***$P<0.001$ vs BSA group.

Stomach extracts were pre-incubated for 1 h with buffer, each polypeptide (3, 31.2 or 62.5 µg), Inhibitor cocktail or BSA (62.5 µg) as positive and negative controls respectively. Then, the substrate casein BODIPY FL (1 µg/ml) was added and the fluorescence intensity measured in a fluorescence plate reader. Results are shown in FIG. 15 as mean % of proteolytic activity±SEM. $P<0.01$, *$P<0.001$ vs BSA group.

Ecotin, Aprin and Y Inhibitor were able to reduce the Ag digestion by intestine extracts while only Y Inhibitor has the capacity to protect the Ag from degradation by stomach extracts. BSA control did not inhibit the proteolytic activity of stomach or intestine extracts in vitro whereas a protease inhibitor cocktail did it.

Commercial pancreatin—a broad-spectrum mixture of proteases produced by the exocrine cells of the porcine pancreas that is usually used for in vitro digestibility analysis—was used to evaluate the susceptibility of the Ag to this content. Pancreatin was pre-incubated for 1 h with buffer, each polypeptide (5, 10, 20 or 40 µg/ml), Inhibitor cocktail or BSA (40 µg) as positive or negative controls respectively. Then, the substrate casein BODIPY FL (1 µg/ml) was added and the fluorescence intensity measured in a fluorescence plate reader. Results are shown as mean % of proteolytic activity±SEM. *P<0.05, P<0.01, *P<0.001 vs BSA group.

The results indicate that all the polypeptides of the invention, in different amounts, can protect the Ag (casein) from digestion by porcine pancreatic extract (FIG. 16).

Altogether, these results indicate that co-administration of the polypeptides of the invention with an Ag by the oral route can protect the Ag passage to the gastrointestinal tract, increasing the half-life of the Ag within cells of the inductive sites: PPs and MLNs.

Example 11—Ecotin Polypeptide in Oral Vaccine Formulation Protects Against *Salmonella* Infection in Mice BALB/c mice were immunized at days 0, 15 and 30, i.g with physiologic solution (SF), Ecotin (100 μg), Ecotin (100 μg)+CT (10 μg), Ecotin (100 μg)+U-Omp19 (150 μg), or intraperitoneally with Ecotin (20 μg) plus Freund Incomplete adjuvant-FIA-(100 μL). Thirty days after last immunization, animals were challenged with virulent Salmonellla 4208 via ip injection. Four days later animals were killed, spleens and livers were homogenized and plated in agar plus streptomycin to evaluate the amount of CFU per gram of tissue.

Results indicate that Ecotin delivered alone, plus CT or FIA cannot induce protection against *Salmonella* infection. However, when co-formulated with the adjuvant U-Omp19 (an unlipidated outer membrane protein from *Brucella abortus*) and administered orally it induces significant reduction in the amount of CFU at spleen (FIG. 17A) and liver (FIG. 17B) in comparison with SF or Ecotin delivery alone. As it was reported previously that Omp19 alone cannot induce protection against *Salmonella* (24) the present results indicate that Ecotin when co-formulated with Omp19 is a good Ag for a vaccine formulation against *Salmonella*.

REFERENCES

1. Takahashi, I., T. Nochi, Y. Yuki, and H. Kiyono. 2009. New horizon of mucosal immunity and vaccines. *Curr Opin Immunol* 21:352-358.
2. Gallichan, W. S., and K. L. Rosenthal. 1996. Long-lived cytotoxic T lymphocyte memory in mucosal tissues after mucosal but not systemic immunization. *J Exp Med* 184:1879-1890.
3. He, X. W., F. Wang, L. Jiang, J. Li, S. K. Liu, Z. Y. Xiao, X. Q. Jin, Y. N. Zhang, Y. He, K. Li, Y. J. Guo, and S. H. Sun. 2005. Induction of mucosal and systemic immune response by single-dose oral immunization with biodegradable microparticles containing DNA encoding HBsAg. *J Gen Virol* 86:601-610.
4. Kim, S. Y., H. J. Doh, J. S. Ahn, Y. J. Ha, M. H. Jang, S. I. Chung, and H. J. Park. 1999. Induction of mucosal and systemic immune response by oral immunization with *H. pylori* lysates encapsulated in poly(D,L-lactide-co-glycolide) microparticles. *Vaccine* 17:607-616.
5. Pavot, V., N. Rochereau, C. Genin, B. Verrier, and S. Paul. 2012. New insights in mucosal vaccine development. *Vaccine* 30:142-154.
6. Mestecky, J., M. W. Russell, and C. O. Elson. 2007. Perspectives on mucosal vaccines: is mucosal tolerance a barrier? *J Immunol* 179:5633-5638.
7. Holmgren, J., and C. Czerkinsky. 2005. Mucosal immunity and vaccines. *Nat Med* 11:S45-53.
8. Mowat, A. M. 2003. Anatomical basis of tolerance and immunity to intestinal antigens. *Nat Rev Immunol* 3:331-341.
9. Diamanti, E., B. Ibrahimi, F. Tafaj, E. Mezini, A. Dodbiba, V. Dobi, S. Catone, D. Genovese, P. Simeoni, and L. Fiore. 1998. Surveillance of suspected poliomyelitis in Albania, 1980-1995: suggestion of increased risk of vaccine associated poliomyelitis. *Vaccine* 16:940-948.
10. Reed, S. G., S. Bertholet, R. N. Coler, and M. Friede. 2009. New horizons in adjuvants for vaccine development. *Trends Immunol* 30:23-32.
11. Coffman, R. L., A. Sher, and R. A. Seder. 2010. Vaccine adjuvants: putting innate immunity to work. *Immunity* 33:492-503.
12. Freytag, L. C., and J. D. Clements. 2005. Mucosal adjuvants. *Vaccine* 23:1804-1813.
13. Hill, D. R., L. Ford, and D. G. Lalloo. 2006. Oral cholera vaccines: use in clinical practice. *Lancet Infect Dis* 6:361-373.
14. El-Kamary, S. S., M. B. Cohen, A. L. Bourgeois, L. Van De Verg, N. Bauers, M. Reymann, M. F. Pasetti, and W. H. Chen. 2014. Safety and immunogenicity of a single oral dose of recombinant double mutant heat-labile toxin derived from enterotoxigenic *Escherichia coli*. *Clin Vaccine Immunol* 20:1764-1770.
15. Zhu, Q., J. Talton, G. Zhang, T. Cunningham, Z. Wang, R. C. Waters, J. Kirk, B. Eppler, D. M. Klinman, Y. Sui, S. Gagnon, I. M. Belyakov, R. J. Mumper, and J. A. Berzofsky. 2012. Large intestine-targeted, nanoparticle-releasing oral vaccine to control genitorectal viral infection. *Nat Med* 18:1291-1296.
16. De Smet, R., T. Demoor, S. Verschuere, M. Dullaers, G. R. Ostroff, G. Leclercq, L. Allais, C. Pilette, M. Dierendonck, B. G. De Geest, and C. A. Cuvelier. 2013. Beta-Glucan microparticles are good candidates for mucosal antigen delivery in oral vaccination. *J Control Release* 172:671-678.
17. Kasturi, S. P., I. Skountzou, R. A. Albrecht, D. Koutsonanos, T. Hua, H. I. Nakaya, R. Ravindran, S. Stewart, M. Alam, M. Kwissa, F. Villinger, N. Murthy, J. Steel, J. Jacob, R. J. Hogan, A. Garcia-Sastre, R. Compans, and B. Pulendran. 2011. Programming the magnitude and persistence of antibody responses with innate immunity. *Nature* 470:543-547.
18. Islam, M. A., J. Firdous, Y. J. Choi, C. H. Yun, and C. S. Cho. 2012. Design and application of chitosan microspheres as oral and nasal vaccine carriers: an updated review. *Int J Nanomedicine* 7:6077-6093.
19. Shima, H., T. Watanabe, S. Fukuda, S. Fukuoka, O. Ohara, and H. Ohno. 2014. A novel mucosal vaccine targeting Peyer's patch M cells induces protective antigen-specific IgA responses. *Int Immunol* 26:619-625.
20. Ibanez, A. E., L. M. Coria, M. V. Carabajal, M. V. Delpino, G. S. Risso, P. G. Cobiello, J. Rinaldi, P. Barrionuevo, L. Bruno, F. Frank, S. Klinke, F. A. Goldbaum, G. Briones, G. H. Giambartolomei, K. A. Pasquevich, and J. Cassataro. 2015. A bacterial protease inhibitor protects antigens delivered in oral vaccines from digestion while triggering specific mucosal immune responses. *J Control Release* 220:18-28.
21. Singh, M., and D. O'Hagan. 1999. Advances in vaccine adjuvants. *Nat Biotechnol* 17:1075-1081.
22. Sultzer, B. M. 1972. Genetic control of host responses to endotoxin. *Infection and immunity* 5:107-113.
23. Sultzer, B. M. 1968. Genetic control of leucocyte responses to endotoxin. *Nature* 219:1253-1254.

24. Risso, G. S. et al. 2017. U-Omp19 from *Brucella abortus* is a Useful adjuvant for Vaccine Formulations against *Salmonella* infection in Mice. *Frontiers Immunology*. Volume 8. Article 171.

The invention claimed is:

1. A pharmaceutical composition comprising (i) an adjuvant comprising an immunomodulating and immunostimulating polypeptide having the amino acid sequence set forth in SEQ ID NO. 1, (ii) one or more antigens, and optionally (iii) one or more pharmaceutically acceptable excipients.

2. The pharmaceutical composition according to claim 1, wherein the one or more antigens are is selected from a viral antigen, a bacterial antigen, a fungal antigen, a parasitic antigen, tumor-derived antigens, self-antigens and allergens.

3. The pharmaceutical composition according to claim 1, wherein the composition is in a form selected from an oral composition and a parenteral composition.

4. A method for enhancing or modulating the immune response against one or more antigens in a subject, comprising administering to said subject an effective amount of the pharmaceutical composition of claim 1, wherein the enhanced or modulated immune response is against the one or more antigens present in the pharmaceutical composition.

5. A method for inducing protective immunity to one or more antigens in a subject, comprising administering to said subject an effective amount of the pharmaceutical composition of claim 1, wherein the induced protective immunity is against the one or more antigens present in the pharmaceutical composition.

6. The method of claim 5, wherein the polypeptide comprised in the pharmaceutical composition is an immunomodulating and immunostimulating polypeptide that enhances a half-life of the one or more antigens.

* * * * *